United States Patent [19]

Gallinger et al.

[11] Patent Number: 5,663,481
[45] Date of Patent: Sep. 2, 1997

[54] ANIMAL MODEL OF THE HUMAN IMMUNE SYSTEM

[75] Inventors: Steven Gallinger; Nobumichi Hozumi; John C. Roder, all of Toronto; Jasbir S. Sandhu, Oakville, all of Canada; Baruch Shpitz, Kefar Sava, Israel

[73] Assignee: Mount Sinai Hospital Corporation, Toronto, Canada

[21] Appl. No.: 102,905

[22] Filed: Aug. 6, 1993

[51] Int. Cl.$^6$ .......................... C12N 15/00; A01N 63/00
[52] U.S. Cl. ...................... 800/2; 424/93.7; 800/DIG. 15
[58] Field of Search ............................................. 800/2

[56] References Cited

U.S. PATENT DOCUMENTS

| | | |
|---|---|---|
| 4,772,552 | 9/1988 | Hercend et al. . |
| 5,004,681 | 4/1991 | Boyse et al. . |

FOREIGN PATENT DOCUMENTS

| | | |
|---|---|---|
| 2048406 | 2/1992 | Canada . |
| 0 438 053 A1 | 7/1991 | European Pat. Off. . |
| WO89/12823 | 12/1989 | WIPO . |
| WO91/16910 | 11/1991 | WIPO . |
| WO93/05796 | 4/1993 | WIPO . |

OTHER PUBLICATIONS

Mosier et al Nature 335: 256, 1988.
Murphy et al Eur. J. Immunol. 22:1421, 1992.
Barry et al J. Exp. Med 173:167, 1991.
Mueller Cover Metastases Rev 10: 193, 1991.
Huppes Eur J. Immunol 22:197, 1992.
Saxon J Clin Invest. 87: 658, 1991.
Carlsson J of Immunol. 148(4): 1065, 1992.
Majintgre Eur J. Immul. 21: 1763, 1991.
Murphy Eur. J. Immunol 22: 1421, 1992.
Bay J. Exp. Med. 173: 167, 1991.
Abedi Eur. J. Immunol. 22: 823, 1992.
McCune, J. M. et al., Science 241:1632, 1988.
Abedi, M.R. et al, Eur. J. Immunol. 22:823–828, 1992.
Huppes, W. et al, Eur. J. Immunol. 22:197–206, 1992.
Mosier et al., Nature 335:256–259, 1988.
Kamel–Reid & Dick, Science, 242:1707, 1988.
Lubin et al., Science, 252:427, 1991.
Barry, T.S. et al, J. Exp. Med., 173:167–180, 1991.
Mosier et al., Nature 338:211, 1989.
Carlsson et al, J. Immunol. 148:1065, 1992.
Jicha, D.L. J. Immunol. 11:19–29, 1992.
Tary–Lehmann and Saxon, J. Exp. Med. 175:503–516, 1992.
Pfeffer et al., Curr. Top. Microbiol. Immunol. 152:211, 1989.
Krams et al., J. Exp. Med. 170:1919, 1989.
Torbett et al., Immunol. Rev. 124:139, 1991.
Duchosal et al., Am. J. Path. 141:1097, 1992.
Duchosal et al., Cellular Immunol. 139:468, 1992.
Markham and Donnenberg Inf. & Immun. 60:2305, 1992.
Mazingue et. al., Eur. J. Immunol. 21:1763, 1991.
Smith, C.I.E. et al, Immunol. Rev. 124:113, 1991.
Duchosal et. al. Nature 355:258, 1992.
Dorshkind et al., J. Immunol. 134:3798, 1985.
Sheng–Tanner and Miller, J. Exp. Med. 176:407, 1992.
Murphy et al., Eur. J. Immunol. 22:1421, 1992.
Davies, Clin. Immunol. Immunopath. 60:319, 1991.
Murphy, Proc. Nat. Acad. Sci. USA 89:4481, 1992.
Kamel–Reid et al, Science, 246:1597, 1989.
Charley et al, J. Invest. Dermatol. 94:381, 1990.
Duchosal et al, J. Exp. Med. 172:985, 1990.
Macht et al., Clin. Exp. Immunol. 84:34, 1991.
Saxon et al, J. Clin. Invest. 87:658, 1991.
Greenwood et al, Biochem. J. 89:114, 1963.
Kasai et al., Nature (Lond.), 291:334, 1981.
Mosier et al., Science, 251:791.
Simpson et al., Immun. Rev. 124:97, 1991.
Weiner et al., Cancer Research 51:94, 1991.
Ortaldo et al., J. Exp. Med., 164:1193, 1986.
Mueller et al., Cancer and Metastasis Reviews 10:193, 1991.

*Primary Examiner*—Suzanne E. Ziska
*Attorney, Agent, or Firm*—Bereskin & Parr

[57] ABSTRACT

The present invention relates to a non-human chimeric mammal having characteristics of a functional human immune system and having functional human lymphocytes reconstituted in the mammal's lymphopoietic tissue, particularly the spleen. The invention also relates to a method of preparing a non-human chimeric mammal, having characteristics of a functional human immune system, by engraftment of human peripheral blood leukocytes into an immunocompromised mammal. Use of the chimeric mammal as a model of the human immune system is described.

13 Claims, 17 Drawing Sheets

Log. fluorescence intensity

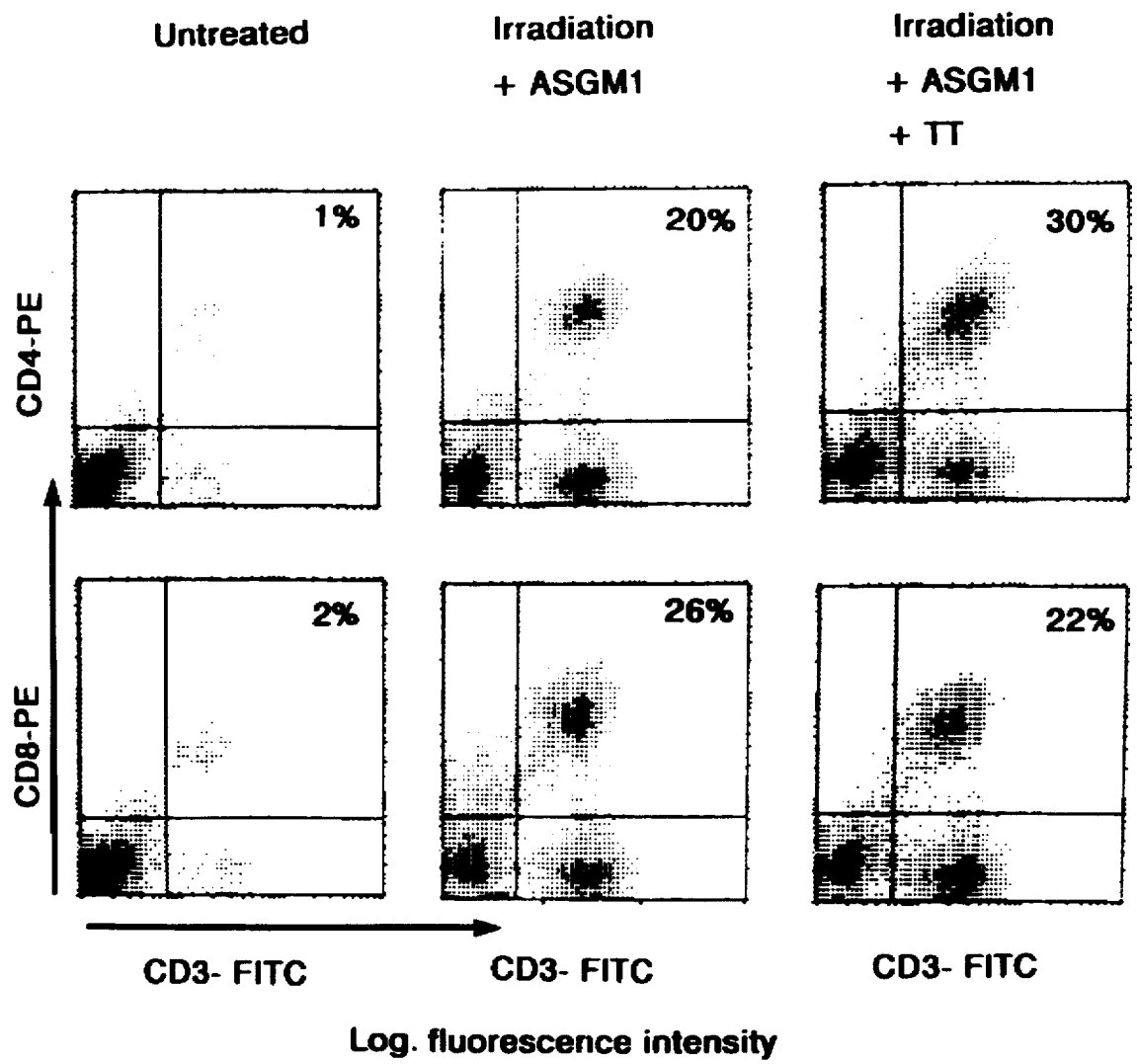

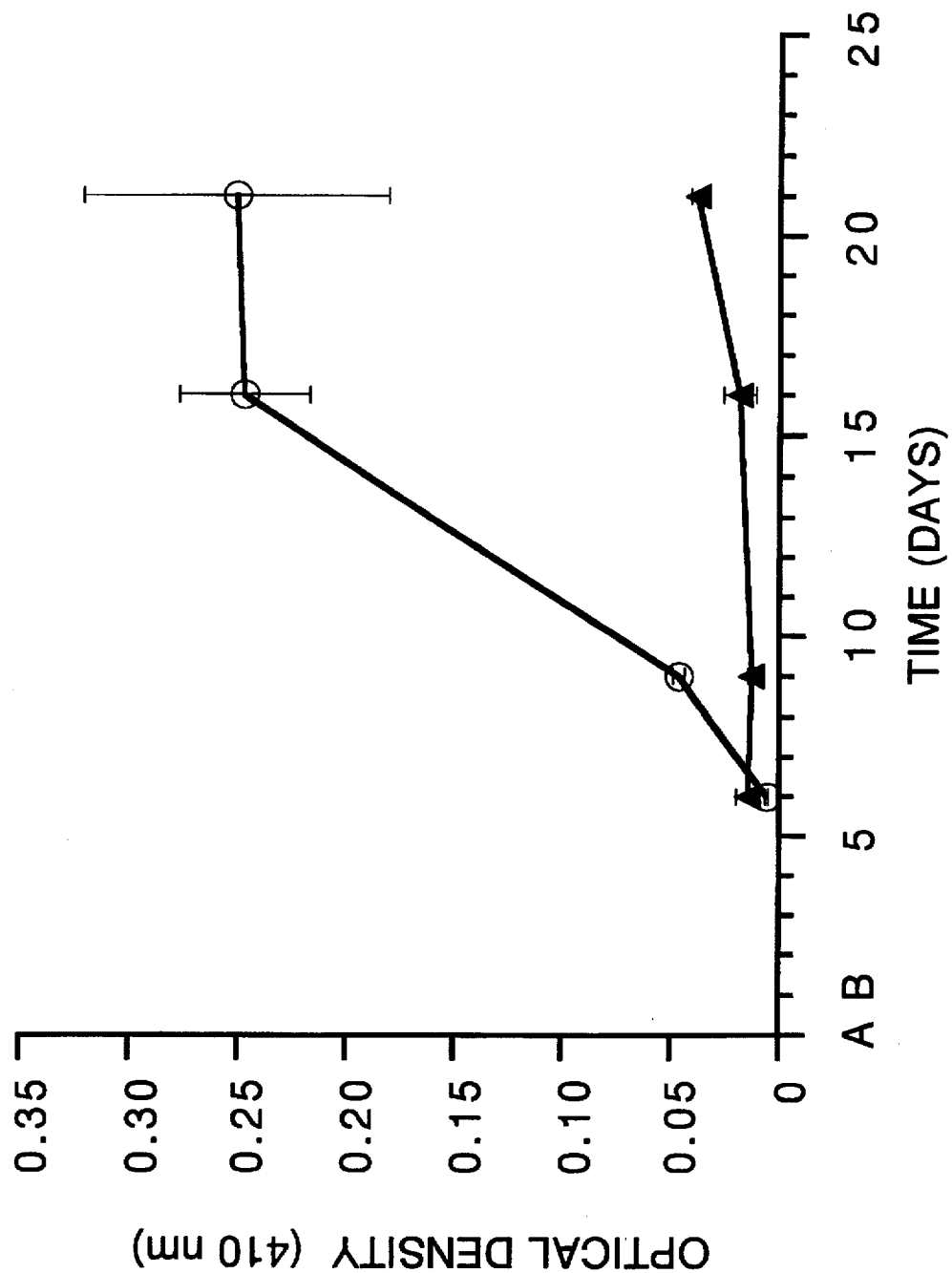

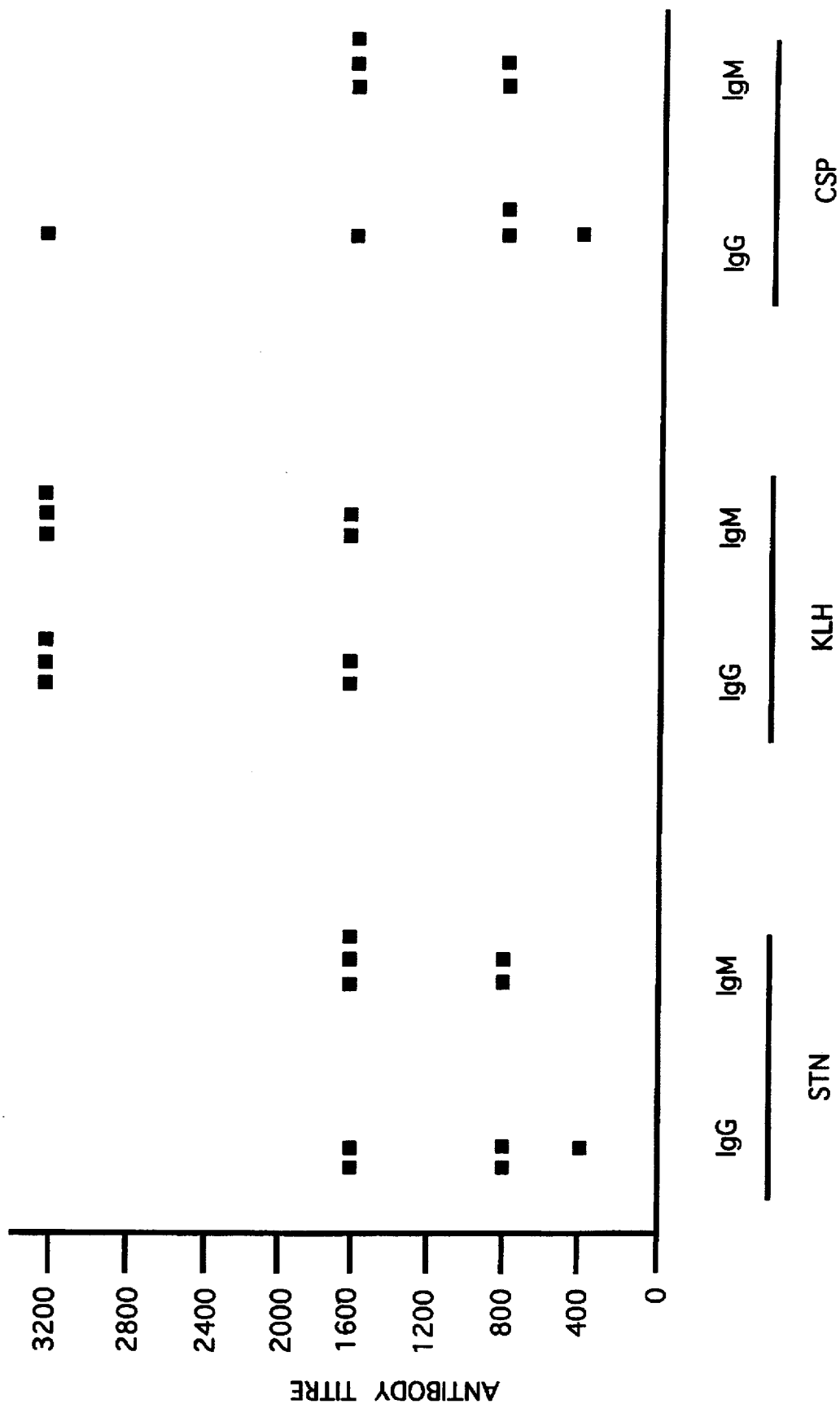

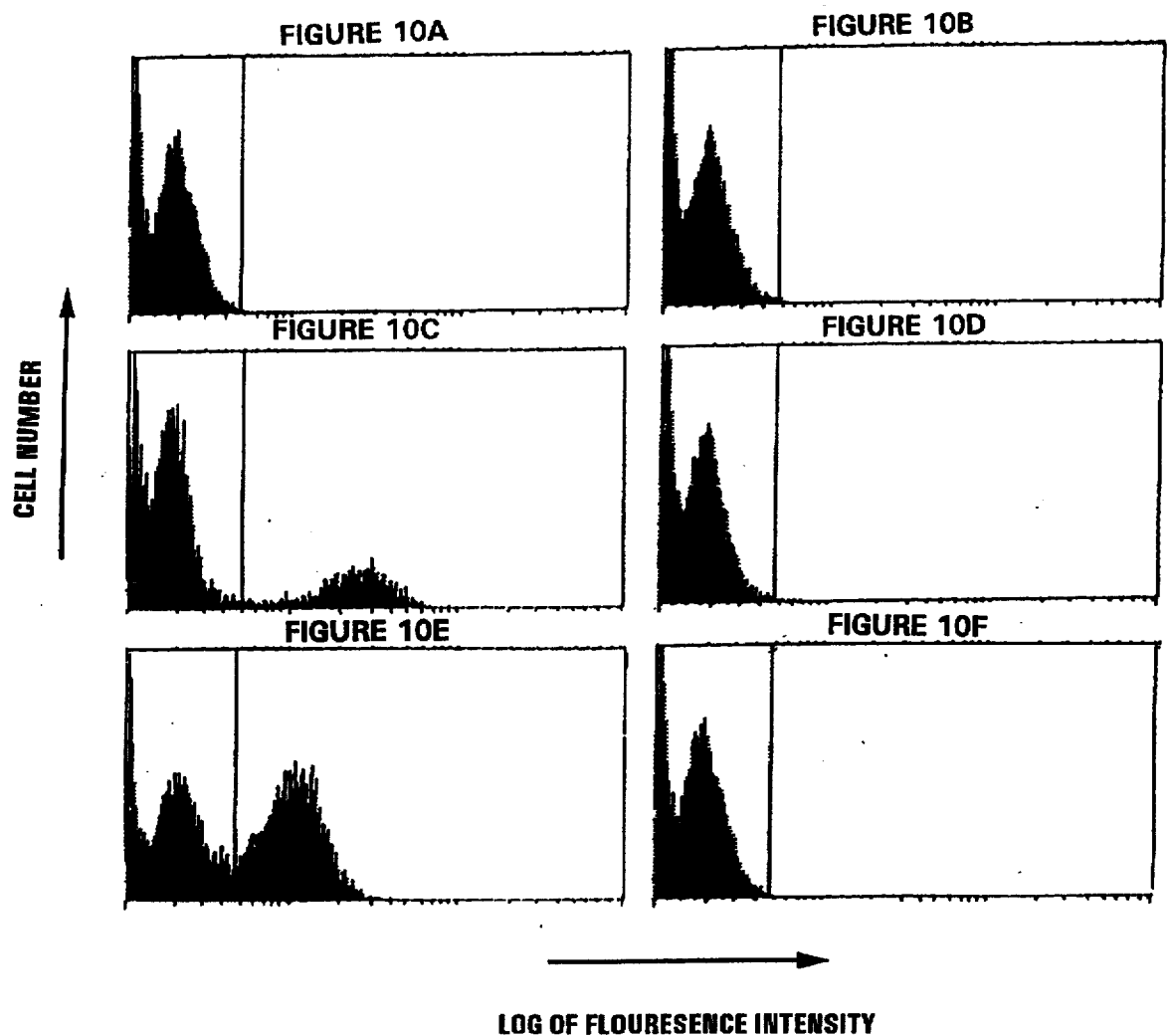

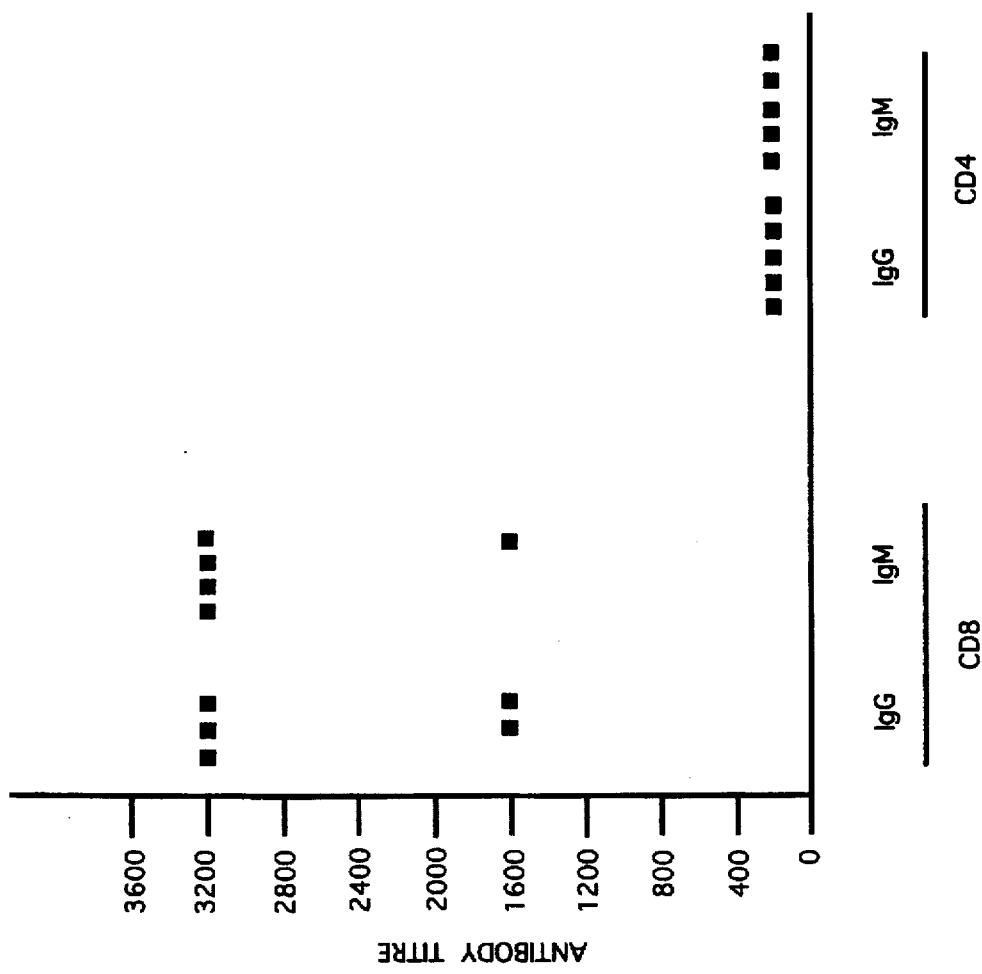

ANIMAL MODEL OF THE HUMAN IMMUNE SYSTEM

FIELD OF THE INVENTION

The invention relates to non-human chimeric mammals having characteristics of a functional human immune system, methods for preparing same, and their use as animal models of the human immune system.

BACKGROUND OF THE INVENTION

The complex interactions of the various cells involved in the generation of the in vivo human immune response can not be adequately reconstituted in vitro. Studies of the human immune system and the development and testing of immunomodulators suitable for human administration have been restricted by the limited ability to experiment with human subjects and the lack of animal models of the human immune system. For example, a major limitation to the preclinical evaluation of novel cancer immunotherapies is the lack of an animal model which contains a functional adult human immune system, having its hemopoietic and lymphopoietic tissues, particularly the spleen, reconstituted with the range of functional cells, including subtypes of T cells, such as T helper cells and cytotoxic cells, B cells and natural killer (NK) cells necessary to reconstitute the complex cellular interactions of the cellular and humoral human immune system.

Several methods have been developed to transfer the human immune system to mice. One approach for generating animal models has involved the use of immunocompromised hosts, which do not mount an effective immune response against the xenogenic hemopoietic cells of the human immune system. The immunocompromised hosts are engrafted with cellular elements of the human immune system.

Reconstitution has been attempted in genetically immunocompromised mice, such as severe combined immunodeficient (SCID) mice and Bg/Nu/XID mice. Homozygous C.B-17 scid/scid mice (SCID mice), congenic partners of BALB/Can, have a severe combined immunodeficiency and lack functional T and B cells (McCune, J. M. et al., Science 241:1632, 1988). SCID mice are unable to mount an effective cellular or humoral response to foreign antigens. Reconstitution has also been attempted in mice in which an immunocompromised state has been induced by for example radiation (Abedi, M. R. et al, Eur. J. Immunol. 22:823, 1992), and cytotoxic drugs (Huppes, W. et al, Eur. J. Immunol. 22:197, 1992).

The strategies that have been used for preparing mice reconstituted with the human immune system involve the transplantation of human fetal tissue (McCune et al., Science 241:1632, 1988), injection of human peripheral blood lymphocytes (PBLs) (Mosier et al., Nature 335:256, 1988), and transfer of bone marrow (Kamel-Reid & Dick, 1988; Lubin et al 1991) into immunodeficient mice such as SCID and beige nude mice.

More particularly, McCune et al (Canadian Patent Application No. 2,048,406 and Science 241: 1632, 1988) engrafted SCID mice with solid implants of fetal human tissue, such as lymphoid tissue, thymus, spleen, bone marrow and hematopoietic stem cells. Fragments of tissue or cells from fetal liver and thymus were introduced into SCID mice. Human lymphocytes were detected in recipient mice, but human cells did not reconstitute host lymphopoietic tissue and were not detected in the host thymus or spleen.

McCune et al also pre-treated the SCID mice with either fractionated courses of irradiation or an anti-asialoglycoprotein antibody (anti-ASGM1), a rabbit antiserum against murine NK cells and macrophages, to at least partially ablate endogenous hematopoietic cells prior to implant of the xenogenic tissue. However, human T cells were only transiently detected in the host peripheral blood and did not appear to home to the host spleen, thymus or lymph nodes. Human IgG production required the introduction of human lymph nodes into the SCID mice.

SCID mice have also been engrafted with post-natal thymus tissue following pretreatment with either radiation or administration of anti-ASGM1, a rabbit antiserum against murine NK cells and macrophages (Barry, T. S. et al, J. Exp. Med. 173:167, 1991). Treatment with anti-ASGM1 promoted thymus engraftment, T and B lymphopoiesis and production of mouse immunoglobulin in the SCID mice. However, only rare CD4+ and CD8+ cells were detected in the spleen.

Mayo et al (PCT Application No. WO91/16910) transplanted SCID mice with human lymph nodes and fetal long bone but did not identify homing of human lymphocytes to the spleen.

An alternative technique for reconstituting mice, developed by Mosier et al, does not require the procurement of human fetal tissues (Mosier et al, Nature 335:256, 1988 and PCT No. WO 89/12823). The Mosier protocol involves injecting adult peripheral blood leukocytes (PBL) into the peritoneal cavity of SCID mice to yield mice referred to as human-peripheral blood leukocytes-SCID (Hu-PBL-SCID) mice.

There are several limitations to the Hu-PBL-SCID model, as originally described by Mosier et al. Initially Mosier et al reported a high level of human lymphocytes in the host spleen. However, this high level of splenic engraftment was subsequently attributed to non-specific binding of the antibodies used to differentiate the human cells from mice splenic cells (Mosier, Nature, 338:211, 1989). Others have also been unable to achieve high levels of splenic reconstitution following the method of Mosier et al when rigorous controls were employed to eliminate non-specific antibody staining (Carlsson et al, J. Immunol. 148:1065, 1992). Jicha, D. L. (J. Immunol. 11:19, 1992), also failed to detect human cells in the spleens of Hu-PBL-SCID mice prepared by the Mosier protocol.

Following the Mosier protocol, the level of human PBLs engrafted in the mice is often low and quite variable. Human T cell engraftment in the lymphoid organs of the Hu-PBL-SCID mice is also significantly limited during the early post-reconstitution period as human PBLs appear to remain predominantly in the peritoneal cavity during the first weeks after reconstitution (Mosier et al., Nature 335:256, 1988; Tary-Lehmann and Saxon, J. Exp. Med. 175:503, 1992; Pfeffer et al., Curr. Top. Microbiol. Immunol. 152:211, 1989; Krams et al, J. Exp. Med. 170:1919, 1989; Torbett et al., Immunol. Rev. 125:139, 1991; Mosier et al., Nature 388:211, 1989; Duchosal et al., Am. J. Path. 141:1097, 1992). Consequently, it has been difficult to assess the functional activities of the engrafted human cells. Human natural killer (NK) activity in the Hu-PBL-SCID model has also not been demonstrated. Hu-PBL-SCID mice produced by the Mosier protocol do not exhibit significant graft versus host reactions and may live for several years after transplant (Duchosal, Cellular Immunol. 139:468, 1992). Accordingly, the mice produced using the Mosier Hu-PBL-SCID protocol are not useful models for studies of human graft versus host disease.

Not all human immune functions can be induced in the Mosier Hu-PBL-SCID mouse model. For example, while it is possible to induce human secondary immune response to tetanus toxoid, and hepatitis B core antigens (Hbc) (Mosier, PCT No. WO89/12823; Duchosal PCT No. WO 93/05796; Duchosal et al Am. J. Pathol. 141:1097, 1992; Duchosal et al, Am. J. Pathol. 141:1097, 1992), no studies have been published, that clearly demonstrate a human primary immune response in this system. The demonstration of a human primary immune response in a non-human host may be a key factor in demonstrating functionality of the xenogenic immune system in the host.

The induction of a human primary immune response in SCID mice engrafted with human PBLs using the Mosier protocol has been the subject of many investigations but no results have been published that clearly and consistently demonstrate this characteristic function in the mice. For example, Mazingue et. al., (Eur. J. Immunol. 21:1763, 1991) reported a primary immune response to a schistosome antigen in Hu-PBL-SCID mice. However, no data for IgM response specific for this antigen was presented, only two Hu-PBL donors were tested, and a single antigen was tested for primary immune response in this model. Mazingue et al also expressed doubts on the human nature of antibodies detected in the Hu-PBL-SCID mouse serum as the anti-human IgG reagents used reacted with mouse sera also. Markham and Donnenberg (Inf. & Immun. 60:2305, 1992) tried to evoke human primary immune response against keyhole limpet haemocyanin (KLH) in the Hu-PBL-SCID mice, but were unsuccessful.

Abedi et. al. (Eur. J. Immunol. 22:823, 1992) tried to induce human primary immune response in Hu-PBL-SCID mice to hepatitis B surface antigen. However, only two out of the sixteen mice were reported to give IgG and IgM response, and no antibody titre results were published for these animals. The authors of this study subsequently noted that the majority of the mice had failed to respond and that they could not exclude a fortuitous expansion of hepatitis-B specific clones in selected mice (Smith, C. I. E. et al, Immunol. Rev. 124:113, 1991).

Duchosal et. al. (Nature 355:258, 1992) engrafted SCID mice with human PBL from a donor with no detectable anti-Hbc antibody titre. One out of twelve Hu-PBL-SCID mice were reported to produce a weak transient IgM and no IgG response after Hbc immunization. Duchosal et al described the ability of Hu-PBL-SCID mice to mount a low primary response to tetanus toxoid (Duchosal, M. A. et al, PCT No. WO93/05796). Although the donors in that study had not been exposed to the antigen recently, it was not known if the donors had some prior exposure to the antigen. The lack of consistent human primary immune response reported in the studies using the Mosier et. al. (Nature, 335:256, 1988) engraftment procedure may be attributed to the low levels of human lymphocyte engraftment.

Evidence of a primary immune response has also been reported from chimeric mice with double engraftments of human bone marrow and from SCID mice transplanted with human lymph nodes. Reisner (Reisner Y., European Patent Application No. 438,053) reconstituted lethally irradiated BALB/c mice with human bone marrow cells and supportive bone marrow cells from SCID mice and reported a primary immune response to KLH-DNP in two mice. Mayo et al (Mayo, S. et al., PCT No. WO91/16910) transplanted human lymph nodes into SCID mice and immunized the graft with TNP-KLH. Four days later anti-TNP producing cells in the lymph node graft were identified by immunohistology. Human antibody producing cells were not shown to have reconstituted host lymphopoietic tissue.

Functional human T, B and NK cells have not been demonstrated in the Mosier Hu-PBL-SCID model. Only limited engraftment of human lymphocytes in the spleen has been achieved with the Mosier protocol discussed above. It is noted that SCID mice posses high levels of active NK cells (Dorshkind et al., J. Immunol. 134:3798, 1985) which can represent a barrier to lymphoid allografts (Sheng-Tanner and Miller, J. Exp. Med. 176:407, 1992) as shown recently (Murphy et al., Eur. J. Immunol. 22:1421, 1992). Pre-treatment with radiation or anti-ASGM1 prior to transplant has been reported to increase engraftment of human lymphocytes, although the reports have provided conflicting results. Low doses of total body irradiation of SCID mice (up to 4 Gyg) have been reported to have minimal effect on engraftment or development of graft versus host disease (GVHD), whereas proliferation of human cells was reported to increase by treatment with anti-mouse IgM (Huppes, W. et al, Eur. J. Immunol. 22:197–206, 1992). Prior irradiation of SCID mice has been reported to increase human IgG levels in the first month after transplant of the Hu-PBL (Duchosal, Am. J. Pathol. 141:3097, 1992). Prior irradiation may cause a slightly more rapid appearance of human IgG in the serum, but does not appear to potentiate repopulation of human cells in the mouse (Smith, C. I. et al, Immunol. Rev. 124:113, 1991). Pre-treatment of mice with anti-ASGM1 has been reported to increase the number of human cells in the spleen one month after engraftment (Murphy, W. J. et al Eur. J. Immunol. 22:1421, 1992). However, the results were variable with 8 out of 28 mice having no detectable human cells in the spleen and the remainder having levels ranging from 1 to 48%.

Human lymphocytes have been detected in the spleen of Hu-PBL-SCID mice by reaction with the human leukocyte common antigen CD45 (Huppes, W. et al, Eur. J. Immunol. 22:197, 1992). In particular, the presence of human T cells has been detected using the CD3, CD4 and CD8 markers (Huppes, 1992, supra; Davies, Clin. Immunol. Immunopath. 60:319, 1991; Murphy, Proc. Nat. Acad. Sci. USA 89:4481, 1992). Human NK cells (CD16+) have only been detected in the peritoneal cavity of the Hu-PBL-SCID mice, the site of injection of the Hu-PBL, and functionality in lysing specific targets has not been determined for these NK cells (Torbett, B. E. et al, Immunol. Rev. 124:,139, 1991).

Animal models of the human immune system are expected to be particularly useful for the evaluation of the effect of drugs on the human immune system, for the development of therapeutics and immunizing compositions and vaccines. Such models would also be useful for testing methods of preventing, treating, enhancing or suppressing an immune response and for treating diseases, such as cancer or infection by pathogenic organisms.

SCID mice reconstituted using lymphocytes have been used to study infectious diseases (McCune et al, 1990, Cannon et al 1190, McCune et al 1991, Okano et al, 1990, Mazingue et al, Eur. J. Immunol. 21:1763, 1991) tumors (Kamel-Reid et al, Science, 246:1597, 1989; Charley et al, J. Invest. Dermatol. 94:381, 1990) autoimmunity (Krams et al, J. Exp. Med. 170:1919, 1989; Duchosal et al, J. Exp. Med. 172:985, 1990; Macht et al., Clin. Exp. Immunol. 84:34, 1991) and primary immunodeficiency (Smith et al, Immunol. Rev. 125:113, 1990 and; Saxon et al, J. Clin. Invest. 87:658, 1991).

SUMMARY OF THE INVENTION

The present inventors have determined that treatment of SCID mice with a protocol of combined low dose irradiation and anti-ASGM1 antibody prior to transplantation with human peripheral blood leukocytes (Hu-PBL) results in rapid homing and consistent engraftment of high levels of functional Hu-PBL in the host spleen. The level of engraftment of Hu-PBL in the host tissues, particularly the spleen, is higher than that achieved heretofore and is higher than would be expected based upon the results previously achieved with either irradiation or anti-ASGM1 pretreatments alone (see Example 1 and FIG. 1).

The reconstituted spleen of the SCID mice were also shown to comprise important subtypes of human lymphocytes, including CD3+, CD4+ and CD8+ T cells, CD19+, CD20+ and HLADR+ B cells, CD16/56+ NK cells and the rare CD11b+ and CD57+ cells.

Importantly, the inventors have not only shown rapid homing and engraftment of Hu-PBL in the spleen, but have also demonstrated the functionality of the engrafted cells in the human immune response. A primary and secondary immune response was consistently demonstrated shortly after engraftment against a number of defined antigens inoculated in vivo. Human functional NK cells from the host spleen were also demonstrated by specific lysis of human NK cell targets. Human T cell functionality was shown by direct evidence in engrafted cells by a secondary immune response to tetanus toxoid antigen and by a proliferative response to phytohemagglutinin (PHA). Human microphage functionality was demonstrated by showing an effect on the human immune response of the chimeric mammals resulting from the specific depletion of human macrophages.

The SCID animals prepared using the combined irradiation and anti-ASGM1 protocol develop graft versus host disease (GVHD) rapidly after engraftment, usually within 2 to 5 weeks of engraftment. The lifespan of the chimeric mammals following engraftment is generally less than one month, on average 25 days, following which they succumb to GVHD. The animals develop ruffled fur and a wasted appearance and exhibit pathology of the liver and lungs.

Broadly stated the present invention relates to a non-human chimeric mammal, obtained by engraftment of human peripheral blood leukocytes into a non-human immunocompromised mammal, and having characteristics of a functional human immune system. The chimeric mammals are generally characterised by functional human lymphocytes, reconstituted in the mammal's lymphopoietic tissue, in particular the spleen. The non-human chimeric mammals are also capable of mounting a human primary and secondary humoral immune response and a cellular immune response to a preselected antigen. The non-human chimeric mammal generally has at least 70% reconstitution of human leukocytes in the spleen and has a functional human T, B and NK cells in the spleen.

The invention further relates to a method of preparing a non-human chimeric mammal comprising: (a) isolating peripheral blood leukocytes from a human donor; (b) obtaining an immunocompromised mammal depleted of functional T and B lymphocytes (c) treating the immunocompromised mammal with irradiation and with an antibody directed to the mammal's natural killer (NK) cells to substantially deplete the mammal's NK cells; (d) transplanting the human peripheral blood leukocytes into the treated immunocomprimised mammal and; (e) maintaining the immunocompromised mammal for a sufficient period of time to obtain a chimeric mammal having at least 70% reconstitution of functional human leukocytes, for example T and B cells and macrophages in the spleen.

The invention also relates to cells and cellular products and tissues isolated from the chimeric mammal of the invention.

The invention also contemplates a method of preparing antibodies to an antigen capable of eliciting an immune response in a human comprising preparing a chimeric mammal of the invention; immunizing the chimeric mammal with the antigen; and isolating human antibodies which bind to the antigen from the chimeric mammal.

The invention also contemplates a method of preparing monoclonal antibodies to an antigen capable of eliciting an immune response in a human comprising preparing a chimeric mammal of the invention; immunizing the chimeric mammal with the antigen; obtaining antibody producing cells from the chimeric mammal; immortalizing the cells to produce hybridomas; screening the hybridomas for production of antibodies which bind to the antigen.

The invention further relates to a method of determining the response of the human immune system to a substance capable of or suspected of inducing an immune response in humans comprising preparing a chimeric mammal of the invention administering the substance to the chimeric mammal; and determining the human immune response to the substance by assaying for human antibodies to the substance, assaying for the substance, examining the pathology of the chimeric mammal and/or examining the proliferation, function and activation of human T, B and NK cells and macrophages in the chimeric mammal.

A method of determining the response of the human immune system to an infectious agent or fractions thereof is also provided comprising preparing a chimeric mammal of the invention administering the infectious agent or fraction thereof to the chimeric mammal; and determining the human immune response to the infectious agent or fraction thereof by assaying for human antibodies to the infectious agent or fraction thereof, assaying for the infectious agent or fraction thereof, examining the pathology of the chimeric mammal and/or examining the proliferation, function and activation of human T, B and NK cells and macrophages in the chimeric mammal.

A method of assaying for a substance that affects human graft versus host disease comprising preparing a chimeric mammal of the invention; treating the chimeric mammal with a substance suspected of affecting human graft versus host disease; and determining the effect of the substance by examining the pathology of the chimeric mammal.

The invention further relates to a method of determining the response of the human immune system to a human tumour comprising preparing a chimeric mammal of the invention; introducing a sample of a human tumour into the chimeric mammal; and determining the human immune response to the tumour by assaying for human antibodies to the tumour, examining the pathology of the chimeric mammal; and/or examining the proliferation, function and activation of human T, B and NK cells and macrophages in the chimeric mammal.

The invention further relates to a method of assaying for a substance that affects the human immune response comprising preparing a chimeric mammal of the invention; inducing an immune response to a preselected antigen in the chimeric mammal; administering a substance suspected of affecting the human immune response; and determining the effect of the substance by assaying for human antibodies to the preselected antigen, examining the pathology of the chimeric mammal; and/or examining the proliferation, function and activation of human T, B and NK cells and macrophages in the chimeric mammal and comparing to a control chimeric animal which has not been administered the substance.

The invention further relates to a method of assaying for a substance that affects the human immune response to an infectious agent comprising preparing a chimeric mammal of the invention; introducing the infectious agent into the chimeric mammal; administering a substance suspected of affecting the human immune response to the infectious agent; and determining the effect of the substance by assaying for human antibodies to the infectious agent, examining the pathology of the chimeric mammal; and/or examining the proliferation, function and activation of human T, B and NK cells and macrophages in the chimeric mammal and comparing to a control chimeric animal which has not been administered the substance.

The invention further relates to a method of assaying for a substance that affects the human immune response to a human tumour comprising preparing a chimeric mammal of the invention; introducing a sample of a human tumour into the chimeric mammal; administering a substance suspected of affecting the human immune response to the tumour; and determining the affect of the substance by assaying for human antibodies to the tumour, examining the pathology of the chimeric mammal; and/or examining the proliferation, function and activation of human T, B and NK cells and macrophages in the chimeric mammal and comparing to a control chimeric animal which has not been administered the substance.

The invention further relates to a method of assaying for a substance which modulate human allogenic graft rejection comprising providing a chimeric mammal of the invention obtained by engrafting human PBL from a first human donor into an immunocompromised host; transplanting the chimeric mammal with a graft from a second donor; administering a substance suspected of modulating human allogenic graft rejection; and determining the affect of the substance by examining the pathology of the chimeric mammal; and/or examining the proliferation, function and activation of human T, B and NK cells and macrophages in the chimeric mammal and comparing to a control chimeric animal which has not been administered the substance.

BRIEF DESCRIPTION OF THE DRAWINGS

Further details of the invention are described below with the help of the examples illustrated in the accompanying drawings in which:

FIG. 6A depicts the results of flow cytometry of human CD3+, and CD4+ lymphocytes in the spleens of chimeric Group1 Hu-PBL-SCID mice;

FIG. 6B depicts the results of flow cytometry of human CD3+ and CD4+ lymphocytes in the spleens of chimeric Group 4 Hu-PBL-SCID mice;

FIG. 6C depicts the results of flow cytometry of human CD3+ and CD4+ lymphocytes in the spleens of chimeric Group 4 Hu-PBL-SCID mice boosted with TT;

FIG. 6D depicts the results of flow cytometry of human CD3+ and CD8+ lymphocytes in the spleens of chimeric Group1 Hu-PBL-SCID mice;

FIG. 6E depicts the results of flow cytometry of human CD3+ and CD8+ lymphocytes in the spleens of chimeric Group 4 Hu-PBL-SCID mice;

FIG. 6F depicts the results of flow cytometry of human CD3+ and CD8+ lymphocytes in the spleens of chimeric Group 4 Hu-PBL-SCID mice boosted with TT;

FIG. 8 is a graph showing kinetics of human IgG anti-KLH response in chimeric SCID mice; Stn human antibody response in chimeric SCID mice;

FIG. 9 is a graph showing an anti-KLH, CSP and Stn human antibody response in chimeric SCID mice;

FIG. 10A is a FACS profile of human CD4 lymphocytes isolated from the spleens of SCID mice;

FIG. 10B is a FACS profile of human CD8 lymphocytes isolated from the spleens of SCID mice;

FIG. 10C is a FACS profile of human CD8 lymphocytes isolated from the spleens of chimeric SCID mice;

FIG. 10D is a FACS profile of human CD8 lymphocytes isolated from the spleens of chimeric SCID mice depleted in CD8;

FIG. 10E is a FACS profile of human CD4 lymphocytes isolated from the spleens of chimeric SCID mice;

FIG. 10F is a FACS profile of human CD8 lymphocytes isolated from the spleens of chimeric SCID mice depleted in CD4;

FIG. 11 is a graph showing a human anti-KLH antibody response in chimeric SCID mice depleted of either CD4 or CD8 lymphocytes; and, FIG. 12 is a graph showing a human anti-KLH response in chimeric SCID mice of the invention and mice prepared by the Mosier protocol.

DETAILED DESCRIPTION OF THE INVENTION

Figure 1A:
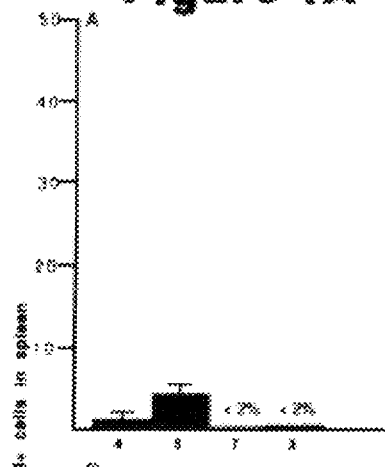
FIG. 1A is a bar graph showing the percentage of human T cells in the spleens of mice receiving no treatment.
Figure 1B:
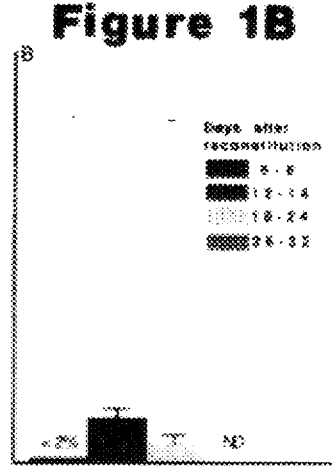
FIG. 1B is a bar graph showing the percentage of human T cells in the spleens of mice pretreated with 25 ml anti-ASGM1.
Figure 1C:
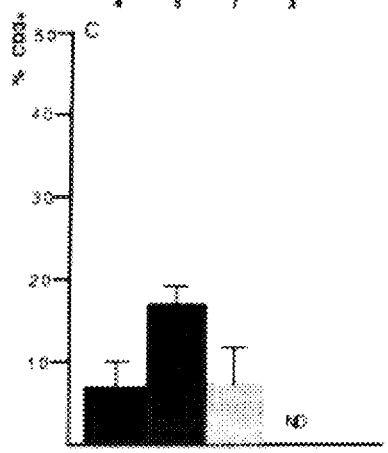
FIG. 1C is a bar graph showing the percentage of human T cells in the spleens of mice that received 3 Gy radiation prior to PBL injection.
Figure 1D:
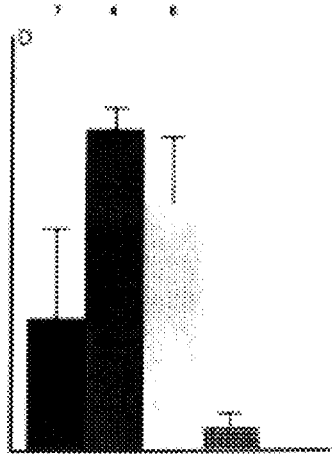
FIG. 1D is a bar graph showing the percentage of human T cells in the spleens of mice that received radiation+25 ml anti-ASGM1 i.p. on the day prior to reconstitution and every 5 to 7 days after PBL injection.

A. Method for Preparing Non-Human Chimeric Mammal

As hereinbefore mentioned the present invention relates to a method of preparing a non-human chimeric mammal comprising: (a) isolating peripheral blood leukocytes from a human donor; (b) treating an immunocompromised mammal with 2–6 Gyg irradiation and with an antibody directed to the immunocompromised mammal's natural killer (NK) cells to substantially deplete the mammal's NK cells; (c) transplanting the human peripheral blood leukocytes into the treated immunocompromised mammal and; (d) maintaining the immunocompromised mammal for a sufficient time, preferably 10 to 15 days, to obtain a chimeric mammal having functional human lymphocytes reconstituted in the chimeric mammal's lymphopoietic tissue, with preferably at least 70% human cell reconstitution of the chimeric mammal's spleen. In a preferred embodiment the immunocompromised mammal is a SCID mouse and the antibody is anti-ASGM1.

Hu-PBL may be isolated from a sample of human whole blood or from buffy coat preparation. Red blood cells may be removed by lysis in hypotonic solution and PBL may be further purified from the sample following known techniques. For example, PBLs may be separated by Ficoll-Hypaque centrifugation (Pharmacia, Pistaway, N.J.). One embodiment of the invention provides for the use of Hu-PBLs enriched in human NK cells. An NK-enriched sample of PBL may be obtained by depleting macrophages and B cells by plastic adherence followed by passage over nylon wool to yield an enriched sample with approximately 20% CD16+/CD56+ cells.

The Hu-PBLs may be transplanted into the host by injection, incision or via catheter. Preferably the human PBL are injected intraperitoneally into the host. A dose of 3.3 to 5.0×10$^7$ PBLs/mouse is preferred for engraftment of SCID mice by the method of the invention.

Immunocompromised mammals which may be considered as candidates for use in the present invention are those immunocompromised mammals lacking functional T and B lymphocytes. Preferably, suitable mammals are functionally the same or equivalent to the homozygous C.B-17 acid/scid mice (SCID mice), which have a severe combined immunodeficiency and lack functional T and B cells as a result of a genetic defect in the ability of the lymphoid lineage to differentiate and mature from a progenitor cell. Examples of suitable immunocompromised mammals include SCID mice; SCID horses; SCID beige mice deficient in T, B and NK cells; nude xid. beige mice (Bg/Nu/XID) deficient in T, B and Nk cells, and Rag mice deficient in B and T cells.

The immunocompromised mammal may be treated with a combination of radiation and specific antibodies to the mammal's NK cells. The present inventors have surprisingly shown that the combined pretreatment protocol of the invention significantly improves short term functional human PBL reconstitution and results in rapid engraftment of functional T, B and NK cells and macrophages in immunocompromised mammals.

The dose of radiation to be administered to the host will depend on the size of the host and its susceptibility to radiation, but should be sufficient to deplete the host's immune cells without killing the host. A dose in the range of 2–4 Gyg, preferably 3 Gyg, may be used for pretreatment of SCID mice. The antibody for use in pretreating the immunocompromised mammal may be selected for specificity against the mammal's NK cells. In a preferred embodiment the antibody also reacts with the mammal's macrophages. Anti-ASGM1 or NK1, preferably anti-ASGM1 are suitable antibodies for use in the pretreatment of immunocompromised mice, preferably SCID mice. 15 to 30 µl, preferably 20 to 25 µl of antibody may be used for a mouse.

It will be appreciated that the dose of radiation and the amounts of antibody administered will depend upon the size and susceptibility of the host. The most appropriate pretreatment regime for a particular immunocompromised mammal may be determined by carrying out a preliminary assay to determine the doses and amounts which provide a reduction in amount of functional NK cells in the immunocompromised mammal. Suitable assays for functional mammalian NK cells are described below. Mammalian functional NK cell activity should be reduced from 0 to 10%, preferably 0 to 5%, most preferably 0 to 2%, of normal levels.

In a preferred embodiment of the method of the invention SCID mice are pretreated with between 10 and 35 µl, preferably 20 µl, anti-ASGM1 antibody, administered intraperitoneally one day prior to engraftment and with 3 Gyg radiation from a $^{137}$Cs source immediately prior to engraftment. In a further preferred embodiment of the invention SCID mice are pretreated with between about 10 and 35 µl, preferably 25 µl, anti-ASGM1 antibody, administered intraperitoneally one day prior to engraftment and every 5–7 days following engraftment, and with 3 Gyg radiation from a $^{137}$Cs source immediately prior to engraftment.

B. Characterisation of Non-Human Chimeric Mammals

As noted above, the present invention further relates to a non-human chimeric mammal, obtained by engraftment of human peripheral blood leukocytes into a non-human immunocompromised mammal, and having characteristics of a functional human immune system. The chimeric mammals are generally characterised by functional human lymphocytes, reconstituted in the mammal's lymphopoietic tissue, in particular the spleen. The non-human chimeric mammal generally has at least 70% human lymphocytes in the spleen and has functional human T, B and NK cells in the spleen. The non-human chimeric mammals are also capable of mounting a human primary and secondary humoral immune response and a cellular immune response to a preselected immunogen.

In particular, the chimeric mammals of the present invention show rapid and consistent homing and engraftment of human cells in the spleen as demonstrated by the high percentages of human lymphocytes in the spleen shortly after engraftment. By 12 to 14 days after engraftment the spleen is comprised of about 70 to 90%, on average 80%, human CD45+ cells, with at least 25%, preferably 25–75% CD3+ T lymphocytes. In an embodiment of the invention CD3+ human T cells make up approximately 40% of the spleen cells of a non-immunized mammal. Human TcRab+ cells comprise 35–60% preferably 37–57% of the spleen cells, or 47% on average. Human TcRag+ cells comprise 1–5%, preferably 1.5–3.5% of the spleen cells, or 2.4% on average. CD16/56+ cells comprise 5–15, preferably 6–10% of the spleen cells. CD20+ cells comprise, 10–25%, preferably 12–22%, or 17.2% on average of the spleen cells. In a preferred embodiment cells having the following cell surface antigens are also present: CD4+, CD8+, CD19+, HLA DR+, CD116 and CD57+. The cells of the peritoneal cavity comprise 48–68% CD3+ T cells.

The presence of human lymphocytes in the haemopoietic and lymphopoietic tissues of the chimeric mammals may be confirmed by techniques known in the art. For example the presence of human leukocytes may be detected by reacting a sample of the haemopoietic, lymphopoietic or other tissue with labelled antibodies against human leukocyte cell surface antigens. Samples of spleen, thymus, blood, lymphatic tissue, peritoneal fluid, liver, ling, gut etc. may be removed from the chimeric mammal for testing for the presence of human leukocytes.

Suitable antibodies for the detection of human leukocytes include those antibodies specific for the human cell surface antigens CD3, CD4, CD8, CD16, CD56, CD14, WT31 (TcRab), CD19, HLA DR, CD20, CD45 and CD56. The antibodies may be labelled with various enzymes, fluorescent materials, luminescent materials and radioactive materials. Examples of suitable enzymes include horseradish peroxidase, biotin, alkaline phosphatase, β-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include radioactive phosphorous $^{32}P$, iodine $I^{125}$, $I^{131}$ or tritium.

Radioactive labelled materials may be prepared by radiolabeling with $^{125}I$ by the chloramine-T method (Greenwood et al, Biochem. J. 89:114, 1963), the lactoperoxidase method (Marchalonis et al, Biochem. J. 124:921, 1971), the Bolton-Hunter method (Bolton and Hunter, Biochem. J. 133:529, 1973 and Bolton Review 18, Amersham International Limited, Buckinghamshire, England, 1977), the iodogen method (Fraker and Speck, Biochem. Biophys. Res. Commun. 80:849, 1978), the Iodo-beads method (Markwell Anal. Biochem. 125:427, 1982) or with tritium by reductive methylation (Tack et al., J. Biol. Chem. 255:8842, 1980).

Known coupling methods (for example Wilson and Nakane, in "Immunofluorescence and Related Staining Techniques", W. Knapp et al, eds, p. 215, Elsevier/North-Holland, Amsterdam & New York, 1978; P. Tijssen and E. Kurstak, Anal. Biochem. 136:451, 1984) may be used to prepare enzyme labelled materials. Fluorescent labelled materials may be prepared by reacting the material with umbelliferone, fluorescein, fluorescein isothiocyanate, dichlorotriazinylamine fluorescein, dansyl chloride, derivatives of rhodamine such as tetramethyl rhodamine isothiocyanate, or phycoerythrin.

The labelled antibodies may be detected in host tissue and bodily fluids, such as spleen, blood, liver, lung, thymus, bone marrow, lymph nodes and peritoneal fluid by methods known in the art, including immunohistology at the level of light or electron microscopy. Human cells labelled with antibodies to human cell surface antigens as described above may be quantitated, for example, by flow cytometry or fluorescence activated cell sorting (FACS). For quantitation, single cell suspensions may be prepared from host tissue or bodily fluids, particularly blood, spleen, thymus, lymph, liver and peritoneal fluid. Preferably red blood cells are lysed prior to quantitation of the human leukocytes. Fluorescently labelled human cells may be quantitated by flow cytometry, for example on an EPIC-C flow cytometer (Coulter Electronics). Stained or fluorescently labelled human cells may be analyzed, separated and quantitated using a fluorescence-activated cell sorter (FACS) such as the Becton Dickenson FAC Star Plus.

Assessment of engraftment with human cells may also be confirmed by assaying host lymphopoietic tissues for the presence of human enzymes, for example glucose phosphate isomerase (GPI). Glucose phosphate isomerase may be assayed as generally described in Chambers et al (Proc. Natl. Acad. Sci. USA 89:1026, 1992). The human isoenzyme hGPI can be distinguished by differences in mobility from the GPI isoenzyme of other mammals, such as mice (Chambers, C. A. et al, 1992, supra.

The chimeric mammals of the present invention have engrafted cells of the human immune system which are functional in vivo. The chimeric mammals of the invention have human T lymphocytes engrafted in the spleen which exhibit levels of functionality comparable to normal human T lymphocytes.

The presence of functional human T cells may be confirmed by assaying for a secondary immune response to a T-dependent antigen. The chimeric mammals of the invention are capable of mounting a secondary immune response to a T-dependent antigen boost and producing specific immunoglobulin at levels comparable to those produced in the blood of boosted human subjects.

A secondary immune response to a T-dependent antigen boost may be detected by techniques known in the art. The initial antigen exposure of the human cells may occur in vivo in humans, in vitro prior to engraftment of the Hu-PBL, or in vivo in the chimeric mammals. The chimeric mammals of the invention may be boosted with the antigen and the specific human antibody response subsequently measured by an immunoassay, such as an enzyme-linked immunosorbent assay (ELISA), employing the antigen and an antibody specific for human immunoglobulin.

The present inventors have shown that chimeric SCID mice of the invention are able to mount an in vivo positive secondary immune response against tetanus toxoid (TT) antigen to produce anti-TT antibody in the serum at levels comparable to those elicited in humans in vivo in response to a similar antigenic boost. The chimeric SCID mice of the invention boosted with TT exhibited a CD4:CD8 ratio of greater than one and the percentage of CD3+ cells in the spleen increased to a range of from 58 to 73%, average 64%. The boosted mice were further characterised by having spleens comprised of 30–53%, average 40%, CD4+ cells and 22–25%, average 22%, CD8+ cells.

The presence of functional T cells may be confirmed by the ability of the spleen cells to exhibit an in vitro proliferative response to phytohemagglutinin (PHA). Cell samples form the reconstituted chimeric mammals may be assayed for the presence of an in vitro proliferative response using techniques known in the art. Cells may be incubated, preferably on irradiated autologous human feeder layers, with PHA and the proliferative response subsequently determined by the incorporation of radioactive metabolic precursors, such as tritiated thymidine. For example, the present inventors have demonstrated a PHA proliferative response of splenocytes from chimeric Hu-PBL-SCID mice of over 40 fold over controls not incubated with PHA. This level of proliferative response is comparable to that of normal human leukocytes.

The chimeric mammals of the invention also have functional CD4+ helper T cells. The presence of functional CD4+ cells may be demonstrated by selectively ablating CD4+ cells in the reconstituted mammals and assaying for the ability of the mammals to mount a response to a T-dependent antigen. CD4+ cells may be selectively ablated for example by treatment with antibodies directed against human CD4. For example, the present inventors depleted CD4+ cells by pretreating chimeric SCID mice just prior to engraftment with mouse $IgG_{2a}$ anti-human CD4. These mice were no longer able to mount the specific antibody response to TT described above. Accordingly, the chimeric mammals of the invention have engrafted functional T cells, including CD4+, cells in the spleen, which show functionality at levels similar to that of normal human leukocytes.

Human B cells may be detected in the spleens of chimeric mammals of the invention using antibodies to the cell surface antigens CD19, CD20, and HLA DR, following the procedures described above. The presence of functional human B cells may be inferred from the production of human immunoglobulins and a specific antibody response to a range of antigens. Levels of human IgG may be quantitated in the serum of the chimeric mammals using techniques known in the art, for example using the Kallestad Model QM 300 automated rate nephelometer (Sanofi Pasteur Diagnostics, Montreal, Quebec). The present inventors found levels of human IgG in the range of 1,000–1,800 mg/L, average of 1,438 mg/L in the serum of unstimulated chimeric SCID mice of the invention.

The chimeric mammals of the present invention exhibit a primary humoral immune response to in vivo administered antigens which are capable of eliciting a primary humoral immune response in humans. The primary immune response comprises the production of specific human IgM and IgG antibodies in response to immunization of the chimeric mammals with a range of antigens. For example the present inventors have detected a specific IgM and IgG response to a single immunisation with 50 µg of the following antigens: keyhole limpet haemocyanin (KLH), surface coat protein of circumsporozoite malaria parasite (CSP), and the carbohydrate antigen Stn. The following range of antibody titres were obtained: 400 to 1600 for STN; 1600 to 3200 for KLH and; 400 to 3200 fro CSP. The primary specific human IgG and IgM responses achieved were comparable or superior to those reported from humans in vivo.

Human NK cells may be detected in the spleens of chimeric mammals of the invention using antibodies to the cell surface antigens CD16 and CD56 following the procedures described above. The present inventors found 6–10% human NK cells in the spleens of engrafted mammals by 12 to 14 days after engraftment. The chimeric mammals of the invention thus have functional human NK cells engrafted in their spleen. The presence of functional human NK cells may be determined by the ability of splenocytes to lyse specific cellular targets in cytotoxicity assays. Suitable assays are described for example in Ortaldo, J. R. et al, J. Exp. Med. 164: 1193 1986. Specific cellular targets for human NK cells include the following tumor cell lines: K562; derived from a patient with chronic myelogenous leukemia; MBL2, a Moloney virus-transformed cell line; FEMX a human melanoma cell line; MOLT-4 cells and; fresh human tumor cells obtained from patients with cancer. The present inventors have shown the presence of functional human NK cells, capable of 48% specific lysis of K562 and MOLT-4 cells in vitro at an effector/target ratio of 50:1, in the spleens of chimeric SCID mice. The level of lysis was equal to that observed with control human PBL at the same effector/target ratio. Thus, splenocytes from the reconstituted SCID mice of the invention show NK functional activity comparable to that of normal human PBL at the same effector to target cell ratios.

The chimeric mammals of the invention are further characterised by the presence of functional human macrophages. The presence of functional human macrophages may be investigated by assaying for the effect on the human immune response of the chimeric mammals of treatment with a specific antibody to human macrophages, such as an antibody to the macrophage cell surface marker CD14. For example the present inventors have found that depletion of CD14+ cells decreased the titre of specific IgM produced in response to immunisation with KLH.

The chimeric mammals of the present invention are further characterised by the rapid onset of graft versus host disease (GVHD) within 2 to 5 weeks of engraftment. The lifespan of the chimeric mammals following engraftment is generally less than one month. The present inventors have shown that chimeric SCID mice of the invention generally have a lifespan following engraftment of 21 to 28 days, average 25 days, following which they succumb to GVHD. The presence of GVHD may be detected by the general appearance of the animals, which develop ruffled fur and a wasted appearance and by pathology of the liver and lungs. Histologically, the mice develop accumulations of inflammatory cells in the liver and perivascular infiltrates and intra-alveolar hemorrhages in the lung.

Chimeric mice depleted of human B cells or human macrophages had lessened GVHD and survived for 50 days and 38 days respectively.

C. Method for Isolating Tissues, Cells and Cellular Products from a Non-Human Chimeric Mammal The present invention further provides non-human haemopoietic and lymphopoietic tissue obtained from the chimeric mammals of the invention. Lymphopoietic and hemopoietic tissue samples may be removed by autopsy or biopsy from the chimeric mammal and may be used immediately or stored on ice, frozen, maintained in culture or transplanted into a host. Examples of hemopoietic tissue include bone marrow, blood and liver, and suitable lymphopoietic tissue includes spleen, thymus and lymph nodes.

The present invention further provides human cells isolated from the tissue or bodily fluids of the chimeric mammals of the invention. Accordingly, the invention contemplates human T, B and NK cells and macrophages removed from a non-human chimeric mammal having characteristics of a functional human immune system. It is further contemplated that the human cells isolated from the non-human chimeric mammal may be specifically primed or activated by exposure to a particular antigen, including a disease specific antigen or other activating agent or lymphokine in vivo.

The chimeric mammals of the invention may be utilized for the isolation of specifically primed human B lymphocytes and to prepare cellular products of such B lymphocytes, in particular immunoglobulins, including antibodies of defined specificity.

Antibodies may be produced which are specific to antigens including haptens modified to elicit a human immune response. Examples of antigens which can be used to generate antibodies are synthetic organic molecules, polypeptides, proteins, lipids, saccharides and combinations thereof. The immunogens may be synthetic or naturally occurring and include drugs, hormones, cytokines, surface membrane proteins, enzymes, sugar groups, oligosaccharides and toxins.

Within the context of the present invention, antibodies are understood to include monoclonal antibodies, polyclonal antibodies, antibody fragments (e.g., Fab, and F(ab')$_2$ and recombinantly produced binding partners. The chimeric reconstituted mammals of the invention permit the specific immunisation and boosting of the human immune system in vivo without the usual ethical constraints which have prevented antigen boosting of human subjects. The antigen boost and even the primary immunisation of the human immune system may be performed using the chimeric mammals of the invention.

Polyclonal antibodies may be readily generated by one of ordinary skill in the art from the chimeric mammals of the present invention. Briefly, a selected antigen is used to immunize the chimeric mammal through intraperitoneal, intramuscular, intraocular, or subcutaneous injections, an adjuvant such as Freund's complete or incomplete adjuvant. The initial exposure to antigen may also take place in vivo in the human donor or by exposure of the Hu-PBL in vitro prior to engraftment following the procedures described in Duchosal, M. A. et al, Nature 355:258, 1992. Following the initial immunization or following one or several booster immunizations, samples of serum are collected and tested for reactivity to the antigen in standard assays, examples of which are described below.

Particularly preferred polyclonal antisera will give a signal on one of the assays that is at least three times greater than background. Once the titer of the animal has reached a plateau in terms of its reactivity to the antigen, larger quantities of antisera may be readily obtained either by weekly bleedings, or by exsanguinating the animal.

Monoclonal antibodies may also be readily generated using conventional techniques (see U.S. Pat. Nos. RE 32,011, 4,902,614, 4,543,439, and 4,411,993 which are incorporated herein by reference; see also Monoclonal Antibodies, Hybridomas: A New Dimension in Biological Analyses, Plenum Press, Kennett, McKearn, and Bechtol (eds.), 1980, and Antibodies: A Laboratory Manual, Harlow and Lane (eds.), Cold Spring Harbor Laboratory Press, 1988, which are also incorporated herein by reference).

Briefly, within one embodiment a chimeric mammal of the invention is injected with an antigen. The antigen may be admixed with an adjuvant such as Freund's complete or incomplete adjuvant in order to increase the resultant immune response. Between one and three weeks after the initial immunization the mammal may be reimmunized with another booster immunization, and tested for reactivity to the antigen using standard assays. Once the mammal has plateaued in its reactivity to the antigen, it is sacrificed, and organs which contain large numbers of human B cells such as the spleen and lymph nodes are harvested.

B cells which are obtained from the immunized chimeric mammal may be immortalized by transfection with a virus such as the Epstein bar virus (EBV) (see Glasky and Reading, Hybridoma 8(4):377–389, 1989). Alternatively, within a preferred embodiment, the harvested spleen and/or lymph node cell suspensions are fused with a suitable myeloma cell in order to create a "hybridoma" which secretes monoclonal antibody. Suitable myeloma lines include, for example, NS-1 (ATCC No. TIB 18), and P3X63-Ag 8.653 (ATCC No. CRL 1580).

Following the fusion, the cells may be placed into culture plates containing a suitable medium, such as RPMI 1640, or DMEM (Dulbecco's Modified Eagles Medium) (JRH Biosciences, Lenexa, Kans.), as well as additional ingredients, such as Fetal Bovine Serum (FBS, ie., from Hyclone, Logan, Utah, or JRH Biosciences). Additionally, the medium should contain a reagent which selectively allows for the growth of fused spleen and myeloma cells such as HAT (hypoxanthine, aminopterin, and thymidine) (Sigma Chemical Co., St. Louis, Mo.). After about seven days, the resulting fused cells or hybridomas may be screened in order to determine the presence of antibodies which are reactive against the antigen. A wide variety of assays may be utilized to determine the presence of antibodies which are reactive against the antigen, including for example Countercurrent Immuno-Electrophoresis, Radioimmunoassays, Radioimmunoprecipitations, Enzyme-Linked Immuno-Sorbent Assays (ELISA), Dot Blot assays, Inhibition or Competition Assays, and sandwich assays (see U.S. Pat. Nos. 4,376,110 and 4,186,530; see also Antibodies: A Laboratory Manual, Harlow and Lane (eds.), Cold Spring Harbor Laboratory Press, 1988). Following several clonal dilutions and reassays, a hybridoma producing antibodies reactive against the antigen may be isolated.

Other techniques may also be utilized to construct monoclonal antibodies (see William D. Huse et al., "Generation of a Large Combinational Library of the Immunoglobulin Repertoire in Phage Lambda," Science 246:1275–1281, December 1989; see also L. Sastry et al., "Cloning of the Immunological Repertoire in $Escherichia$ $coli$ for Generation of Monoclonal Catalytic Antibodies: Construction of a Heavy Chain Variable Region-Specific cDNA Library," Proc Natl. Acad. Sci USA 86:5728–5732, August 1989; see also Michelle Alting-Mees et al., "Monoclonal Antibody Expression Libraries: A Rapid Alternative to Hybridomas," Strategies in Molecular Biology 3:1–9, January 1990; these references describe a commercial system available from Stratacyte, La Jolla, Calif., which enables the production of antibodies through recombinant techniques). Briefly, mRNA is isolated from a B cell population, and utilized to create heavy and light chain immunoglobulin cDNA expression libraries in the λImmunoZap(H) and λImmunoZap(L) vectors. These vectors may be screened individually or co-expressed to form Fab fragments or antibodies (see Huse et al. supra; see also Sastry et al., supra). Positive plaques may subsequently be converted to a non-lytic plasmid which allows high level expression of monoclonal antibody fragments from $E.$ $coli$. Duchosal et al, 1992, supra, describe techniques for the construction of Fab combinatorial libraries from Hu-PBL-SCID RNA for cloning human antibodies.

Similarly, binding partners may also be constructed utilizing recombinant DNA techniques to incorporate the variable regions of a gene which encodes a specifically binding antibody. Within one embodiment, the genes which encode the variable region from a hybridoma producing a monoclonal antibody of interest are amplified using nucleotide primers for the variable region. These primers may be synthesized by one of ordinary skill in the art, or may be purchased from commercially available sources. Stratacyte (La Jolla, Calif.) sells primers for mouse and human variable regions including, among others, primers for $V_{H3}$, $V_{Hh}$, $V_{Mc}$, $V_{Hd}$, $C_{H1}$, $V_L$ and $C_L$ regions. These primers may be utilized to amplify heavy or light chain variable regions, which may then be inserted into vectors such as ImmunoZAP™ H or ImmunoZAP™ L (Stratacyte), respectively. These vectors may then be introduced in $E.$ $coli$ for expression. Utilizing these techniques, large amounts of a single-chain protein containing a fusion of the VH and VL domains may be produced (See Bird et al., Science 242:423–426, 1988).

Once suitable antibodies or binding partners have been obtained, they may be isolated or purified by many techniques well known to those of ordinary skill in the art (see Antibodies: A Laboratory Manual, Harlow and Lane (eds.), Cold Spring Harbor Laboratory Press, 1988). Suitable techniques include peptide or protein affinity columns, HPLC or RP-HPLC, purification on protein A or protein G columns, or any combination of these techniques.

Antibodies produced using the chimeric mammal of the invention may be used for diagnostic and therapeutic uses. Antibodies directed to antigens specific to a particular disease state may be used for diagnostic purposes in immunoassays. Therapeutic uses include the specific targeting of disease causing agents or diseased cells to destroy the same.

The subject antibodies may be modified by labelling with a detectable marker, such as an enzyme, for example horseradish peroxidase, alkaline phosphatase, glucose oxidase and galactosidase; radionucleotides or fluorescently markers. The antibodies may also be conjugated to other antibodies to form bispecific antibody conjugates, or to therapeutic agents, such as cytotoxic drugs, for the treatment of cancer, for delivery of the therapeutic agent to the targeted disease causing agent or diseased cells. Preferably, the antibodies may be used in the treatment of tumors, viruses, such as HIV, septicemia, ablation of particular T-lymphocyte receptors and neutralizing viruses or other pathogens.

The chimeric mammals of the invention may also be used in the production of cells of the human immune system and products of these cells, such as lymphokines. For example human T lymphocytes, NK cells and macrophages may be produced and specifically activated in vivo in the chimeric mammals of the invention. Human T cells primed with a specific antigen may be produced, including CD4 helper cells, CD8 suppressor cells, NK cells, cytotoxic T-lymphocytes, antibody dependent cytotoxic cells and tumour infiltrating cells. Preferably, human T-lymphocytes specific for a particular target cell or a particular immunodominant sequence are produced.

D. Methods for Preparing, and Characteristics of Depleted Chimeric Mammals

The role of particular human cell types in the immune response may also be studied by selectively depleting particular human cell types from the chimeric mammal. A cell type bearing a particular cell surface antigen may be selectively depleted, for example, by treating the chimeric mammal with specific antibodies directed against the surface antigen. Surface antigens of the cells of the human immune system are known in the art and have been discussed hereinbefore. The human immune response of the selectively depleted chimeric mammal to a substance known or suspected of inducing an immune response can be studied as described above.

The present invention still further provides chimeric non-human mammals having a reconstituted functional immune system depleted of a particular cell type of the human immune system. Such specifically depleted chimeric animals may be prepared by the method of the invention and comprising the additional step of specifically depleting a cell type(s) of the human immune system. A cell type may be depleted by treating the immunocompromised mammal, preferably prior to engraftment, with specific antibodies to a cell surface antigen(s) expressed by that cell type.

Accordingly, the present invention contemplates chimeric mammals having a functional human immune system, except for a particular cell type such as cells having the following surface antigens CD3, CD4, CD8, CD16, CD56, CD14, WT31 (TcRab), CD19, HLA DR, CD20, CD45 and CD56. For example, the present inventors have treated SCID mice with anti-CD4 or CD8 prior to engraftment with PBL. The specifically depleted chimeric mammals described above may be used to study the role of the cell type particularly depleted. For example depletion of CD4+ cells was determined to abrogate the ability of the Hu-PBL-SCID mice to mount a primary immune response to KLH, whereas depletion of CD8+ cells had no such effect and depletion of human macrophages decreased specific anti-KLH titres.

E. Use of the Chimeric Non-Human Mammals as Models of the Human Immune System

The non-human chimeric mammals of the invention may be used to study the human immune system. As hereinbefore mentioned, the present invention provides a non-human chimeric mammal having characteristics of a functional human immune system and a method for preparing the same. Accordingly, the invention generally provides a non-human model of the human immune system and provides a method of studying the cellular and humoral responses of the human immune system in vivo. Suitable methods for studying particular aspects of the human immune system are discussed in more detail below. However, in general, the human immune response may be studied by preparing the chimeric mammals of the invention and introducing a substance known to be capable of, or suspected of, inducing an immune response in humans or modifying the immune response in humans and determining the human immune response in vivo in the chimeric mammal. The human immune response in the mammalian host may be determined using techniques known in the art and described herein, for example, assaying for human antibodies to the substance, antibody response, proliferation, function and activation of cells of the human immune system, such as T, B and NK cells and macrophages may be monitored.

The chimeric mammals of the invention also provide an in vivo model system for assaying for substances, which are suspected of having an immunomodulating effect on the human immune system. The immunomodulating effect may be immunopotentiating or immunosuppressive. Such substances may be assayed by introducing an antigen or suspected antigen into the chimeric mammal, and administering the substance to a test chimeric mammal, and determining the human immune response to the antigen in the test animal or in control animals lacking the substance.

One embodiment of the present invention provides a method of determining the response of the human immune response to an infectious agent comprising creating a non-human chimeric mammal of the invention; introducing the infectious agent or fractions thereof into the chimeric mammal; and determining the effect of the human immune response on the infectious agent by examining the mammal, the human immune response, or the infectious agent in, or harvested from, the chimeric mammal.

Infectious agents which may be introduced into the chimeric mammals of the invention include human pathogens such as bacteria, viruses, yeasts, fungi, actinomycetes, protozoa and helminths. Suitable fractions of the infectious agents include those fractions which are known to be, or are suspected of being, immunogenic in humans, including protein or peptide fractions isolated from the infectious agent or synthesized by recombinant technology. The infectious agents or fractions thereof may be introduced into the blood stream, tissues or cavities of the mammal. The chimeric mammals having an infectious agent or fraction thereof may be used to study the human immune response to the agent. The cellular and humoral response may be assayed as described herein. The effect of the human immune response in the chimeric mammal on the infectious agent may be monitored for example by survival of the agent or pathological reaction to the agent.

The functioning human immune system in the chimeric mammals of the invention is expected to be particularly useful for research on the Human Immunodeficiency Virus (HIV). In addition to use as a research tool the chimeric mammals of the invention may be used to assay for substances which affect the progression of a human infectious disease, such as Aquired Immunodeficiency Disease, AIDS resulting from HIV infection, and the development of an effective immune response against the causative agent. Such uses include testing of substances which may interfere with the progression of disease or potentiate the human immune response against the causative agent of the disease.

The chimeric mammals of the present invention also provide in vivo models for the development of human vaccines, and the isolated tissues and human cells from the chimeric mammals provide an in vitro model. Antigens may be assayed for potential use in human vaccines by measuring the human immune response to the antigen in the chimeric mammal and the effect of the human immune response on the causative agent of the disease, introduced into the chimeric mammal as generally described above. The chimeric mammals of the invention are expected to be useful as a model system for studying the human response in vivo to human malignancies and for assaying for substances which affect the immune response to the malignant cells. Malignant cells from human tumor samples or from transformed human tumor cell lines may be implanted or injected into the chimeric mammals and the in vivo human immune response to the tumor cells may be studied. Substances may also be introduced into the chimeric mammals, transplanted with human tumor cells, which are suspected of having an affect on the tumor cells or on the human immune response to the tumor cells. In particular, the present invention contemplates an assay for substances which potentiate the human immune response to tumor cells.

The model may also prove useful for the study of lymphocyte activated killer cell and tumor infiltrating lymphocyte trafficking into tumor xenografts. Novel cancer immunotherapies based on human effector cell and tumor cell targeting mediated by bispecific antibodies may also be assessed with the chimeric mammals of the invention (Weiner et al., 1993). In many in vivo immunotherapy experiments, the effects of treatment are usually assessed within 2–3 weeks, as control tumor bearing mice often die from tumor progression within a short period of time. The chimeric mammals of the invention will also provide a useful model for the study of the human immune response to allogenic grafts and for the graft rejection mechanisms of the human immune system. Chimeric mammals may be transplanted with tissue or cells from another animal, particularly from a human. Where the Hu-PBL used to reconstitute the chimeric mammals are obtained from a different donor than the transplanted tissue or cells, then a human immune response will likely be elicited in the chimeric mice against the allogenic transplanted cells. Thus, the invention also provides a model for assaying for substances, including immunosuppressants, which modulate human allogenic graft rejection.

The following non-limiting examples are illustrative of the present invention:

EXAMPLE 1

Engraftment of SCID Mice with Human PBL

SCID Mice

Homozygous C.B-17 scid/scid (SCID) mice were bred and maintained in microisolator cages (original breeding pair gift of Dr. R. Phillips, Hospital for Sick Children, Toronto, Ont.) at the Samuel Lunenfeld Research Institute animal colony. Animals were fed autoclaved food and water and all manipulations were performed under laminar flow. Mice were used when 4–10 weeks old.

Pretreatment of SCID Mice

In some cases, SCID mice were irradiated immediately prior to PBL engraftment. A dose of 3 Gyg-radiation was administered from a $^{137}$Cs source (Gamacell, Atomic Energy of Canada Ltd. Commercial Products). Anti-ASGM1 is a rabbit polyclonal antibody which recognizes murine NK cells and depletes NK activity when injected i.p. (Kasai et al., Nature (Lond.), 291:334, 1981). Some mice were pretreated with anti-ASGM1 (25 µl i.p.) (Wako Chemicals, Dallas, Tex.) 1 day prior to human PBL injection and every 5–7 days following reconstitution. In preliminary experiments, this treatment reduced SCID splenocyte NK activity against $^{51}$Cr-labelled YAC targets from 22% lysis by splenocytes from untreated animals to 0–2% in treated animals at an effector-to-target (E:T) ratio of 50:1. Irradiation alone had no effect on NK activity of SCID mouse splenocytes against YAC targets.

Engraftment of SCID Mice with Human PBLs

Buffy coats, provided by the Canadian Red Cross, or whole blood from volunteers were used in these studies. PBLs were isolated by Ficoll-Hypaque centrifugation (Pharmacia, Pistaway, N.J.) and injected i.p. (3.3–5.0×10$^7$ PBLs/mouse) into SCID mice under sterile conditions. In some cases, SCID mice were injected with NK-enriched PBLs. For these studies, Ficoll-separated PBLs were depleted of macrophages and B cells by plastic adherence followed by passage over nylon wool. The percentage of NK cells following enrichment was approximately twice that of non-enriched PBLs as determined by flow cytometry (~20% CD16$^+$, CD56$^+$ cells in NK enriched fraction).

Pretreatment of SCID mice with radiation plus anti-ASGM1 resulted in rapid, short term human PBL engraftment. A total of 165 mice were engrafted with human PBLs. Group 1 mice (n=19) received no pretreatment. Group 2 mice (n=17) were pretreated with anti-ASGM1 on the day prior to injection of PBLs and every 5–7 days following engraftment. Group 3 mice (n=53) were irradiated prior to engraftment, and Group 4 mice (n=76) were pretreated with radiation plus anti-ASGM1 and received injections of anti-ASGM1 every 5–7 days following engraftment.

Figure 1E:
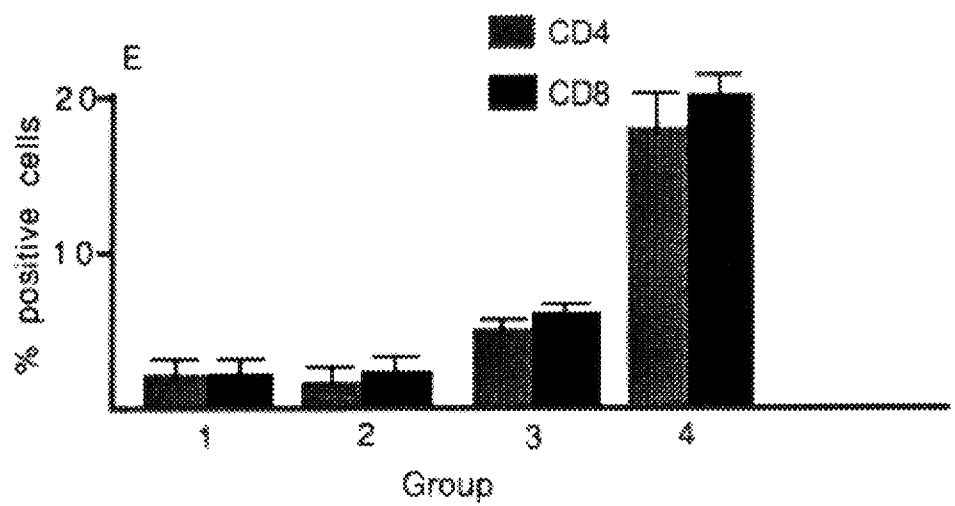

Mice were sacrificed at various times after injection of PBLs and flow cytometry was used to detect human lymphocytes in the mouse spleens as a measure of engraftment. The results, expressed as the percentages of human T cells in the spleens of reconstituted SCID mice, are shown in FIGS. 1A–D. All animals were injected i.p with 3.3–5.0×10$^7$ human PBLs. Group 1 mice (A) received no pretreatment. Group 2 mice (B) were pretreated with 25 ml anti-ASGM1 i.p. on the day prior to reconstitution and every 5–7 days after PBL injection. Group 3 (C) mice received 3 Gy radiation prior to PBL injection. Group 4 (D) mice received radiation+25 ml anti-ASGM1 i.p. on the day prior to reconstitution and every 5–7 days after PBL injection. Animals were sacrificed on the days indicated after engraftment and splenocytes analyzed for the presence of human CD3$^+$ T cells by FCM. Mean±SEM percentages for each group are shown. Numbers below each vertical bar indicate the number of mice in each group. FIG. 1E shows the percentages of CD4$^+$ and CD8$^+$ cells in the spleens of mice in FIGS. 1A–D. Percentages shown are from mice sacrificed on days 12–14.

As can be seen from FIG. 1, engraftment was poor in untreated mice and in mice pretreated with anti-ASGM1 only. Pretreatment of mice with radiation improved reconstitution however the greatest success was found in mice pretreated with radiation plus anti-ASGM1 (Group 4). The highest levels of engraftment, with least variability between mice, was seen 12–14 days after injection of PBLs. Over 80% (43 of 53) of Group 4 mice had greater than 25% CD3$^+$ cells in their spleens and only 6% (3 of 53) had less than 10% CD3$^+$ cells in their spleens at this time. Similar to previous reports (Mosier et al., Nature 335:256, 1988 and; Torbett et al., Immunol. Rev. 124:139, 1991), the CD4CD8 ratio of the human T cells was skewed to <1.0 in most Hu-PBL-SCID mice regardless of the treatment protocol (FIG. 1E).

Several experiments were performed to confirm the high engraftment of human cells in Group 4 Hu-PBL-SCID mice and to show that the high percentage of CD3$^+$ cells in the spleens was due primarily to addition of human cells rather than just depletion of mouse splenocytes. As shown in Table 1, pretreatment of mice with radiation or anti-ASGM1, or both, resulted in a moderate depletion of the numbers of SCID mouse splenocytes whereas Group 4 Hu-PBL-SCID mice had higher numbers of lymphocytes in their spleens compared to normal SCID mice. This provides evidence that large numbers of human lymphocytes engrafted the spleens of Group 4 Hu-PBL-SCID mice.

Human CD3⁺ cells were detected at high levels in the peritoneal cavity of Group 4 Hu-PBL-SCID mice (58.6±10.6%, mean±SEM). CD3⁺ cells were also present in the peripheral blood, liver and lungs of the same Group 4 mice over a broad range of 6.2–65.5% and at low levels in bone marrow (6.1±2.4%) and thymus (1.4±0.4%).

Assessment of Human PBL Engraftment in Hu-PBL-SCID Mice by GLucose Phosphate Isomerase Analysis Splenocytes from control SCID and Hu-PBL-SCID mice prepared as described above were analysed for the presence of human and murine glucose phosphate isomerase (GPI) as generally described in Chambers et al. (Proc. Natl. Acad. Sci. USA 89:1026, 1992). Briefly, red blood cells (RBCs) in spleens were lysed with hypotonic saline and lysates (1×10⁶ cells/sample) were run on cellulose acetate plates (Helena Laboratories, Beaumont, Tex.). The membranes were stained with 1M Tris-Hcl Ph 8.0, containing 10 mg NADP, 75 mg fructose-6-phosphate, 50 U glucose-6-phosphate dehydrogenase, 1.8 phenazine methylsulphate, 10 mg thiazolyl blue (all from Sigma, St. Louis, Mo.) in 1.2% agarose. The levels of human GPI is underestimated due to high GPI activity of any residual mouse RBCs. The assay is sensitive to approximately 3–5% human PBLs.

Figure 2:
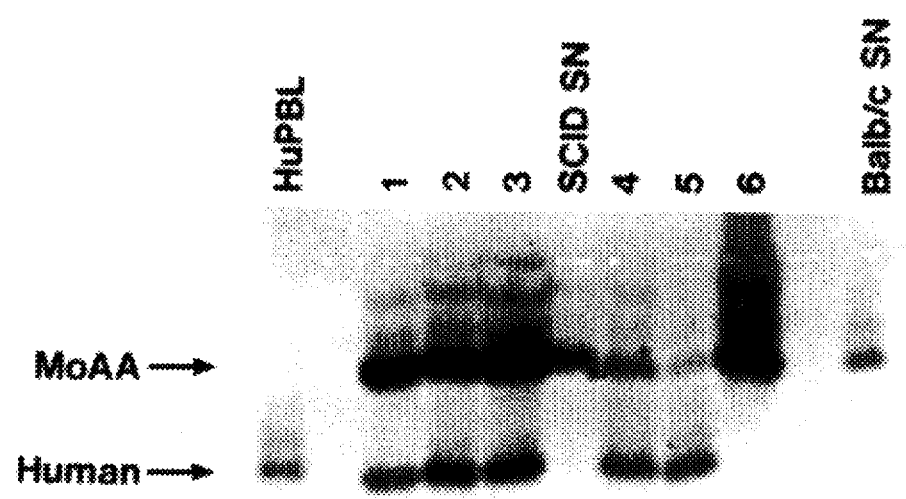
FIG. 2 is a zymogram of human and mouse GPI from spleen lysates.

As shown in FIG. 2, human GPI isoenzyme was present at high levels in the animals from Group 4. FIG. 2 is a zymogram of human and mouse GPI. Spleen lysates were electrophoresed on cellulose membranes and enzymatic activity was detected as described in Chambers, A. C. et al (Proc. Nat. Acad. Sci. USA, 89:1026, 1992). Mouse AA (MoAA) GPI haplotype and human PBL GPI are indicated (arrows). Samples 1–5 are from Group 4 Hu-PBL-SCID mice sacrificed on day 15 following engraftment. Sample 6 is from a Group 1 mouse. Lanes labelled Hu-PBL-SCID SN, Balb/c SN are lysate controls from human PBLs or mouse spleens respectively.

Based on a standard curve established with known proportions of human PBLs and SCID mouse splenocytes, the levels of human GPI in Group 4 animals correlated with the percentage of CD3⁺ cells in the spleens of these mice.

Assessment of Human PBL Engraftment in Hu-PBL-SCID Mice by Flow Cytometry

Hu-PBL-SCID mice, prepared as described above were sacrificed 6–32 days after engraftment and spleens harvested. In some cases, blood, liver, lung, thymus, bone marrow and peritoneal fluid were also analysed for the presence of human PBLs. Single cell suspensions were prepared and red blood cells (RBCs) lysed with hypotonic saline prior to flow cytometry. The following antibodies specific for human cell surface antigens were used: CD3, CD4, CD8, CD3/CD16/CD56 simultest, CD14, WT31 (TCRab) (Becton Dickinson, Mountain View, Calif.) CD20, CD45 (Coulter, Hialeah, Fla.), and TcRgd (T-cell Sciences, Cambridge, Mass.). All antibodies were conjugated with fluorescein isothiocyanate (FITC) or phycoerythrin (PE) except WT31 for which goat-anti-mouse FITC (Coulter) secondary antibody was used. Cells (1–2×10⁵ cells/sample) were incubated with antibodies for 45 minutes on ice followed by three washes with PBS containing 1% fetal calf serum (FCS). At least 5×10³ cells were counted on an EPIC-C flow cytometer (Coulter Electronics). Splenocytes from non-reconstituted SCID mice were frequently tested and were always negative when stained with any of the anti-human lymphocyte markers.

CD45, TcRab, and TcRgd positive cells were demonstrated within splenocytes from engrafted mice as shown in Table 2. Human NK and B cells were also present in the spleens of these mice as detected with a CD16/CD56 simultest antibody and CD20 antibody respectively. These data show the successful engraftment of human T, B and NK cells in Group 4 reconstituted SCID mice in similar proportions to that seen in human blood. In a separate experiment, 6 SCID mice were pretreated with radiation plus anti-ASGM1 then injected with PBLs which had been depleted of macrophages by plastic adherence. When sacrificed on day 13 after engraftment the mean percent CD16⁺ cells in the blood of the 5 mice demonstrating engraftment was 38.4±16.9. Representative flow cytometry showing CD3⁺, and CD16⁺, CD56⁺ cells in the blood of these mice is shown in FIG. 3.

Figure 3A:
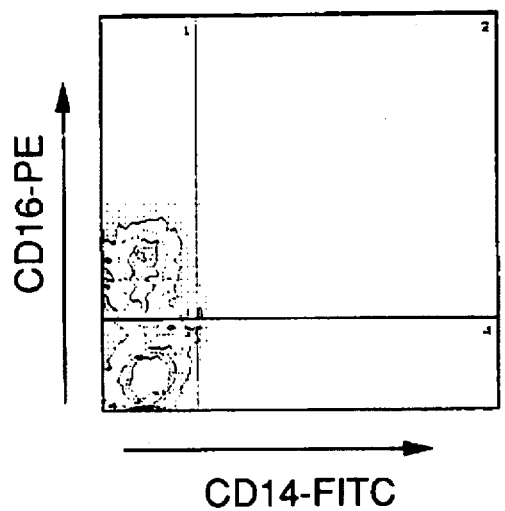
FIG. 3A depicts the results of flow cytometry and shows CD3+, CD16+ and CD56+ cells in the blood of chimeric SCID mice.
Figure 3B:
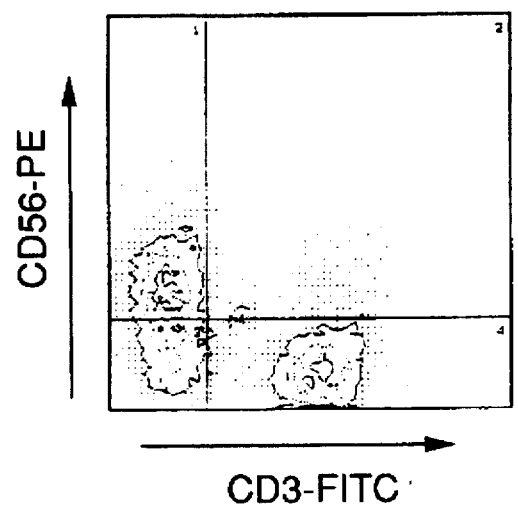
FIG. 3B depicts the results of flow cytometry and shows CD3+, CD16+ and CD56+ cells in the blood of chimeric SCID mice.
Figure 4A:
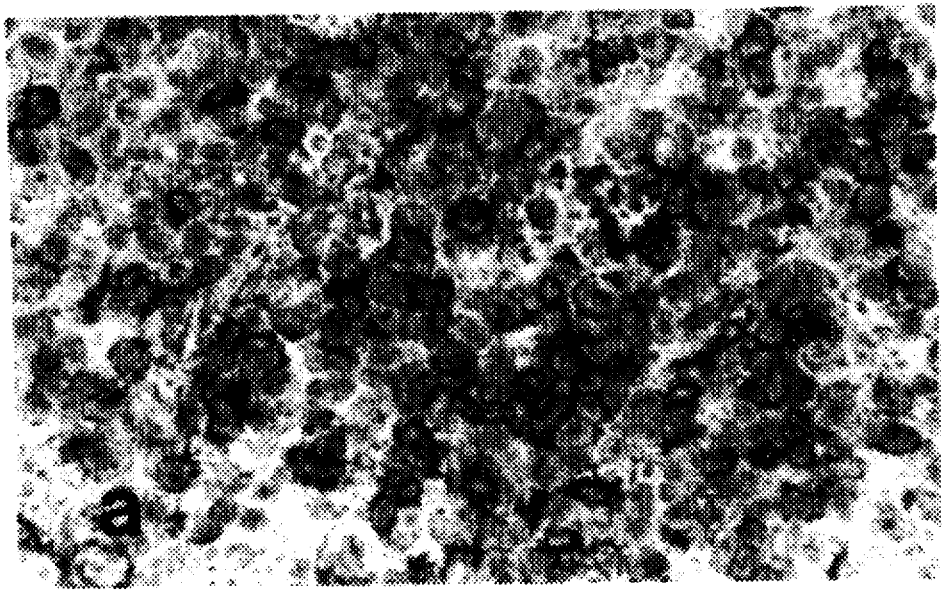
FIG. 4A is a photomicrograph showing immunohistologic staining of chimeric mouse spleens with CD3.
Figure 4B:
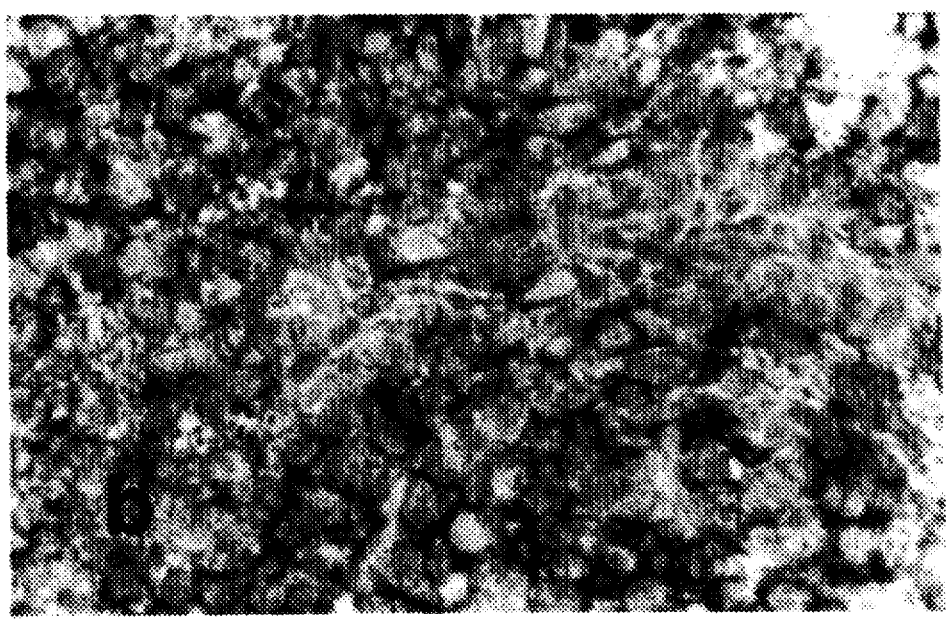
FIG. 4B is a photomicrograph showing immunohistologic staining of chimeric mouse spleens with CD19.
Figure 4C:
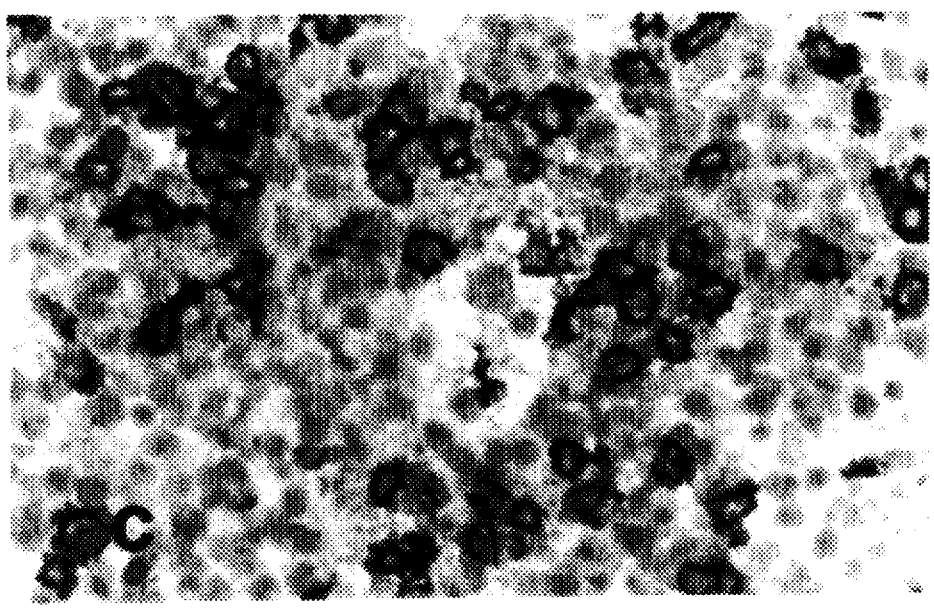
FIG. 4C is a photomicrograph showing immunohistologic staining of chimeric mouse spleens with CD4.
Figure 4D:
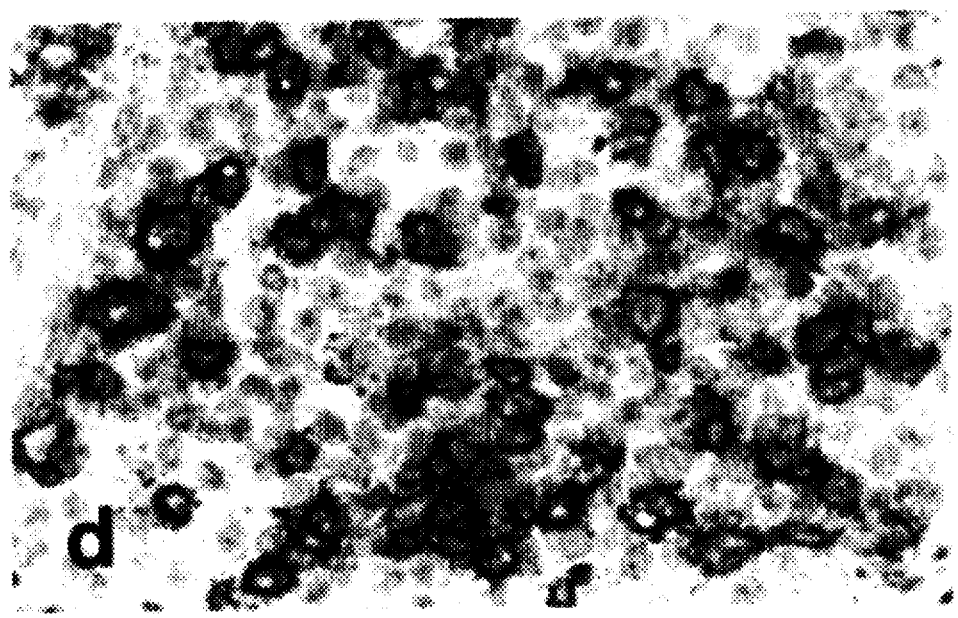
FIG. 4D is a photomicrograph showing immunohistologic staining of chimeric mouse spleens with CD8.

FIG. 3 show CD3⁺ and CD16⁺, CD56⁺ cells in the blood of pretreated Hu-PBL-SCID mice. Flow cytometry of blood from SCID mice pretreated with radiation plus anti-ASGM1 then injected with PBLs which had been depleted of macrophages by plastic adherence. Mice were sacrificed on day 13 after injection of human PBLs. Data from a representative mouse is shown in FIG. 3.

Assessment of Human PBL Engraftment in Hu-PBL-SCID Mice by Immunohistologic Staining Spleens from control and Hu-PBL-SCID mice pretreated with radiation and anti-ASGM1 were embedded in OCT compound (Miles Inc., Elkhart, Ind.) in a cryomould and snap frozen in liquid nitrogen. Frozen sections were cut at 5 mm thickness and dry-mounted on glass slides. Cut sections were allowed to dry overnight at room temperature. Immediately before staining, the slides were fixed in anhydrous acetone for 10 minutes at room temperature and then dried for 5 minutes. The slides were then post-fixed in 10% formol-calcium solution for 10 seconds at room temperature and washed in Tris-buffered saline. Staining was performed using antibodies to the following antigens: CD3, CD4, CD8, CD19, CD20, CD11b, CD57 and HLA-DR (Coulter). The slides were incubated with the primary antibody for 30 minutes in a humid chamber, then washed. The AS/AP Plus® Universal Mouse Kit (Bio/Can Scientific, Mississauga, ONT) was used to detect localization of antibody in the tissue. Negative controls were performed omitting the primary antibody.

Human IgG Hu-PBL-SCID Mice

Further confirmation of the successful engraftment of Group 4 Hu-PBL-SCID mice was obtained by immunohistologic staining. Spleens from Group 4 Hu-PBL-SCID mice sacrificed 12–14 days after engraftment showed positive staining of numerous CD3, CD4, CD8, CD19, CD20 and HLA-DR mononuclear cells. Human CD3, CD4 and CD8 positive T cells and CD19, CD20 and HLA-DR positive B cells were noted in the para-trabecular and peri-vascular areas of the spleen. The majority of these cells were located in the greatly expanded peri-arteriolar lymphoid sheaths. A few CD3, CD4 and many CD8 positive cells were also noted in the cords and sinusoids of the red pulp. Rare positive CD11b and CD57 cells were also detected. Representative sections from Hu-PBL-SCID mice stained with CD3, CD4, CD8 and CD19 antibodies are shown in FIG. 4. FIG. 4 shows human PBL engraftment as demonstrated by immunohistologic staining of Group 4 Hu-PBL-SCID mouse spleens. Mice were sacrificed 12 days after reconstitution and spleens processed for immunohistologic staining. Sections of spleens stained with a) CD3, b) CD19, c)CD4 and d) CD8 (Hematoxylin counterstain; ×500) are shown in FIG. 4. The spleens from control, nonreconstituted SCID mice were negative for human antigens.

Detection of Human IgG

Human IgG was quantitated by the Kallestad Model QM 300 automated rate nephelometer. (Sanofi Pasteur Diagnostics, Montreal, Que.). The lower limit of detection of human Ig with this assay is 35 mg/L. Normal human serum values for IgG are 5600–17,600 mg/L. Levels of human IgG (mean, 1438±224 mg/L) (n=8) were found within one month which were similar to values quoted in the literature in other Hu-PBL-SCID mice (Mosier et al., Nature 335:256, 1988; Krams et al., J. Exp. Med. 170:1919, 1989; Duchosal et al., J. Exp. Med. 172:985, 1990; Davies et al., Clin. Immunol. Immunopathol. 60:319, 1991; Saxon et al., J. Clin. Invest. 87:658, 1991; Duchosal et al., Cell. Immunol. 139:468,: 1992b; Abedi et al., Eur. J. Immunol. 22, 823, 1992; Carlsson et al., J. Immunol. 148, 1065, 1992; Smith et al., Immunol. Rev. 124:113, 1991).

Although most Group 4 Hu-PBL-SCID mice were successfully engrafted, both mouse and human PBL donor variability was observed in the degree of engraftment (Table 3). Some human PBL donors engrafted SCID mice to greater levels than others and variability was observed, albeit to a lesser extent, between the levels of engraftment of different SCID mice injected with PBLs from the same donor.

EXAMPLE 2

Functional Analysis of Human Lymphocyte Populations in the Hu-PBL-SCID Mouse.

Human Lymphocyte Proliferative Response Phytohemagglutinin (PHA)

RBC depleted splenocytes from Hu-PBL-SCID mice, prepared as described in Example 1 ($0.5 \times 10^5$ cells) were incubated with fresh, irradiated (30 Gy) autologous human PBL feeders ($0.5-1.0 \times 10^5$ cells) in RPMI+10% pooled human serum+$5 \times 10^{-5}$M 2-ME in 96 well U-bottomed plates±PHA (1.0–5.0 mg/ml). Replicates of 3–6 wells were used in each experiment. Plates were incubated for 4 days then pulsed with 1 mCi $^3$H-thymidine. After 16 hours, the wells were washed, and incorporation of $^3$H-thymidine (Amersham International, Amersham, UK) was measured in a b counter. Splenocytes from Group 4 mice were capable of an in vitro proliferative response to PHA as shown in Table 4.

Human Lymphocyte Response to Tetanus Toxoid (TT) Boost

Four or five days after PBL injection, mice were injected i.p. with 100 ml TT (Wyeth, Mzrietta, Pa. or Connaught, Willowdale, Ont.). Blood was collected from the tail vein or retro-orbital sinus 6 days after TT injection or by cardiac puncture on day 12 following TT injection. Serum was tested for human anti-TT specific antibodies by enzyme-linked immunosorbent assay (ELISA) generally as described in Melville-Smith et al. (J. Biol. Stand. 11:137, 1983). Briefly, serum samples were incubated in microwells coated with TT (Connaught). Mouse anti-human IgG-alkaline phosphatase was then added, incubated, and unbound conjugate washed off. The bound conjugate was visualized with a phosphatase substrate (Sigma). The extinction was measured with an automated photometer at 410 nm. This assay is sensitive to 0.01 IU/ml human anti-TT antibody.

Figure 5:
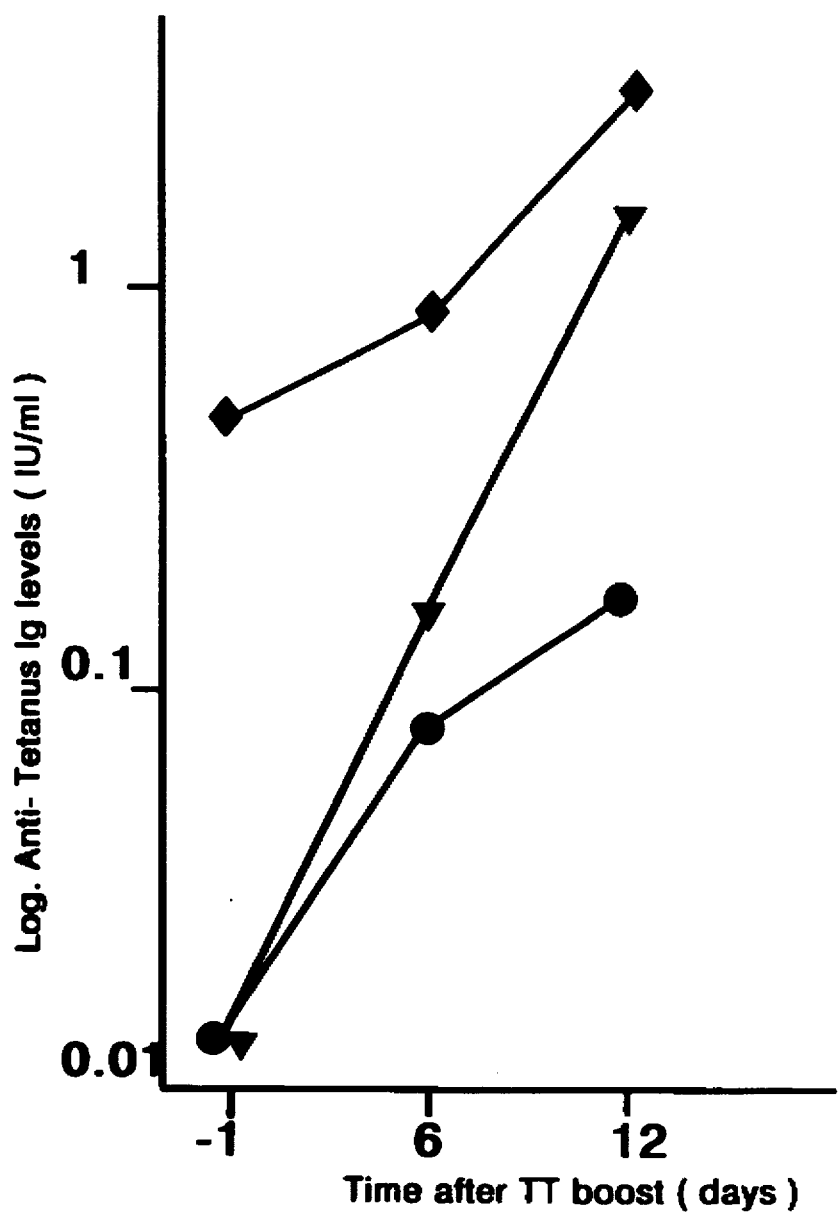
FIG. 5 is a graph showing anti-tetanus toxoid-specific human antibody response in chimeric SCID mice.

The in vivo antibody response to tetanus toxoid was measured as described above. Blood from two donors were used for reconstituion: PBLs from a buffy coat donor whose tetanus immunization status was unknown (donor 1) and, PBLs from a volunteer who received his last tetanus boost 9 years earlier (donor 2). Two SCID mice were pretreated with radiation plus anti-ASGM1 prior to engraftment with PBLs from donor 1. Four mice were reconstituted with PBLs from donor 2, two of which were pretreated with radiation plus anti-ASGM1 and two were untreated. As shown in FIG. 5, mice pretreated with radiation plus anti-ASGM1 had high levels of anti-TT antibody in their serum. FIG. 5 shows the anti-tetanus toxoid-specific human antibody response. Group 4 Hu-PBL-SCID mice reconstituted with human PBLs from a buffy coat (unknown tetanus immunization status) (circles) or a volunteer (last tetanus boost received 9 years previously) (triangles). Mice were bled prior to reconstitution and on day 6 or 12 following an i.p. injection of TT on day 4–5 after PBL injection. Human anti-TT specific Ig levels were measured by ELISA. For comparison, the volunteer was boosted with TT after his PBLs were used for reconstitution and anti-TT Ig levels measured 6 and 12 days later (diamonds).

Mice not pretreated with radiation plus anti-ASGM1 had very low levels of anti-tetanus antibody in their serum when tested 6 or 12 days after the TT boost.

Following reconstitution of mice with PBLs from donor 2, the volunteer was boosted with a usual dose of TT (0.5 ml) and serum anti-TT antibody levels measured. The day 12 response generated in the pretreated Hu-PBL-SCID mice is comparable to the day 6 titer detected in the serum of the donor after boosting.

Splenocytes from TT immunized mice were also analysed for the presence of human CD3, CD4 and CD8 positive cells 12 days after TT injection. Mice pretreated with radiation plus anti-ASGM1, and boosted with TT, showed higher levels of human CD3$^+$ cells and almost normal CD4:CD8 ratios when compared with non-immunized Hu-PBL-SCID mice as shown in FIG. 6. FIG. 6 shows flow cytometry (FCM) of human CD3$^+$, CD4$^+$ and CD8$^+$ lymphocytes in the spleens of Hu-PBL-SCID mice. Representative FCM profiles from Group 1 Hu-PBL-SCID mice (left), Group 4 Hu-PBL-SCID mice (centre) and Group 4 Hu-PBL-SCID mice boosted with TT (right). Mice were sacrificed on day 12 after PBL injection (left and centre panels) or on day 12 after TT boost (16 days after PBL injection, right panel). Splenocytes were double labelled with CD3 FITC/CD4 PE and CD3 FITC/CD8 PE. Note the CD4:CD8 ratio was <1 in the mouse not TT boosted and >1 in the TT boosted animal.

The mean percentage CD3$^+$ cells in 4 pretreated and TT immunized mice was 63.6% (range: 58.2–72.9) and the mean CD4$^+$ and CD8$^+$ cells was 39.8% (range:30.0–52.8) and 23.2% (range: 22.3–24.2) respectively (CD4:CD8 ratio approximately 1.7:1).

Human NK Activity in Hu-PBL-SCID Mouse Splenocytes $10^6$ human NK sensitive K562 and MOLT-4 tumor cell targets were labelled with 100 mCi $^{51}$Cr (Amersham) for 2 hours then washed with RPMI. RBC depleted splenocytes from Hu-PBL-SCID mice were serially diluted in 100 ml complete medium (RPMI+10% FCS) and incubated in triplicates with $5 \times 10^3$ targets in 100 ml in V-bottomed 96 well plates (Nunc, Denmark). After 4 hours, plates were spun and 100 ml supernatant collected. Released $^{51}$Cr in the supernatant was counted in a g-counter and percent specific lysis determined by the formula:

experimental release-spontaneous release×100% maximal release-spontaneous release (maximal release following addition of 10% Triton-X to targets).

Figure 7A:
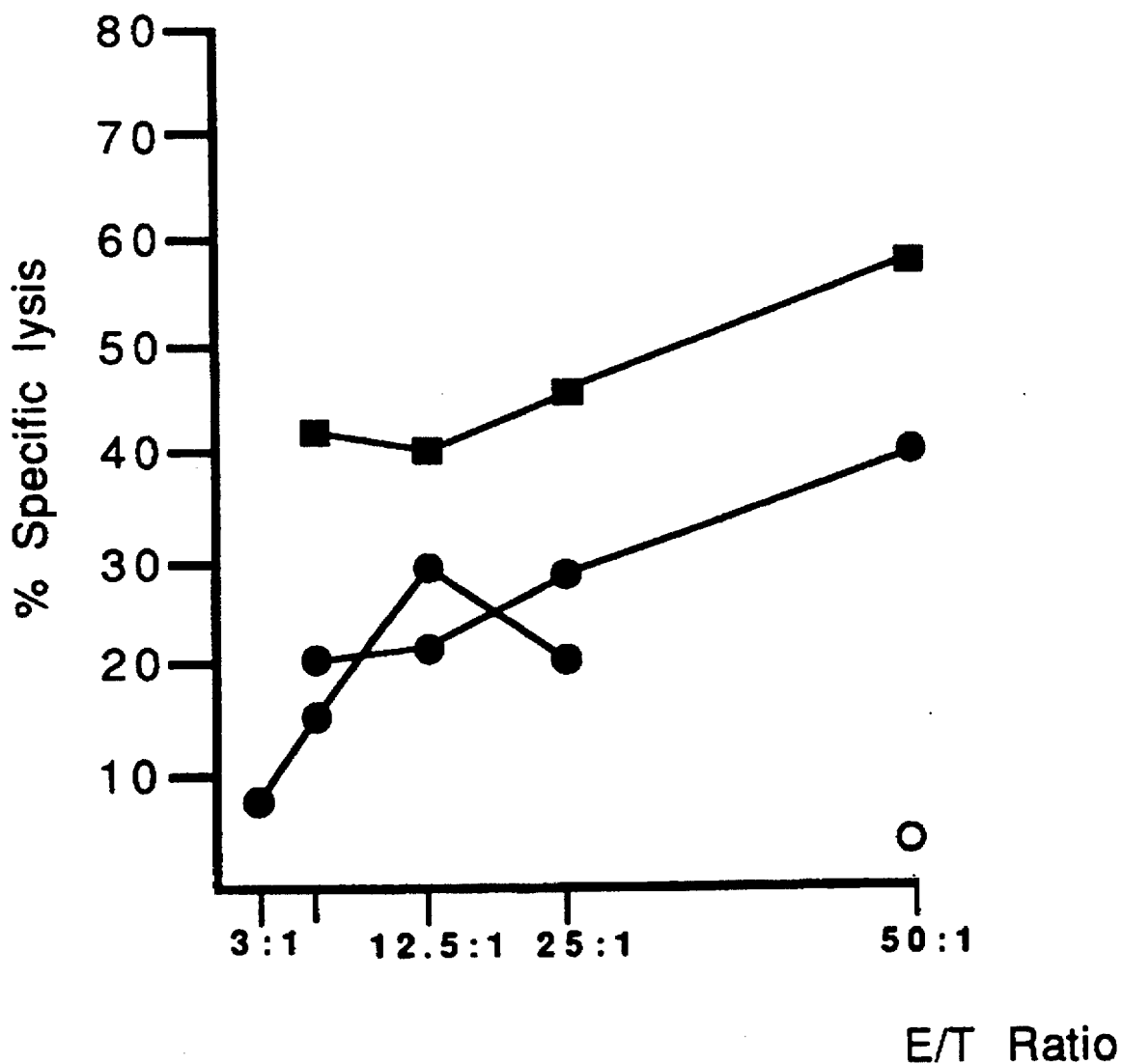
FIG. 7A is a graph showing lysis of human NK sensitive targets by splenocytes of chimeric SCID mice where the splenocytes were incubated with $^{51}$Cr labelled MOLT-4.
Figure 7B:
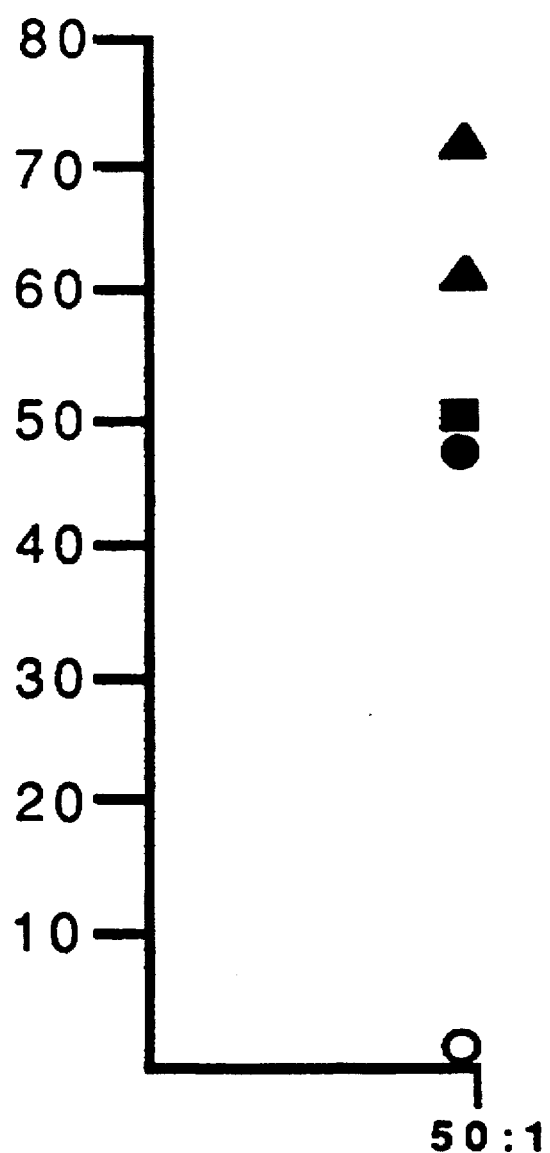
FIG. 7B is a graph showing lysis of human NK sensitive targets by splenocytes of chimeric SCID mice where the splenocytes were incubated with $^{51}$Cr labelled K562.

The function of NK cells was measured in vitro lysis of human NK sensitive targets, K562 and MOLT-4 and the results are shown in FIG. 7. FIG. 7 shows lysis of human NK-sensitive targets by Hu-PBL-SCID splenocytes. SCID mice were pretreated with radiation plus anti-ASGM1, then engrafted with human PBLs. In some cases, PBLs were enriched two-fold for NK cells prior to injection. On day 12 following reconstitution, spleens were harvested, RBCs lysed and splenocytes incubated with $^{51}$Cr labelled MOLT-4 (A) or K562 (B) targets in triplicates at indicated E:T ratios. After 4 h, released $^{51}$Cr was measured and % specific lysis calculated. Solid circle, splenocytes from non-NK enriched Hu-PBL-SCID mice; triangle, splenocytes from NK-enriched Hu-PBL-SCID mice; square, normal human PBLs; open circle, non-reconstituted SCID mice.

As may be seen in FIG. 7, Group 4 Hu-PBL-SCID splenocytes displayed 48% specific lysis of K562 which was equal to that observed with control human PBL effectors at the same E:T ratio. Significant lysis of MOLT-4 was also seen with Group 4 Hu-PBL-SCID splenocytes. In Group 4 Hu-PBL-SCID mice reconstituted with NK-enriched human PBLs, a greater percentage of CD16$^+$ cells were present in the mouse spleens as determined by FCM (mean CD16$^+$ cells, 19.9±3.4%). Splenocytes from these NK-enriched mice displayed even greater lysis of K562. These data confirm the presence of functional human NK cells in Group 4 Hu-PBL-SCID mice.

Graft Versus Host Disease (GVHD) in Group 4 Hu-PBL-SCID Mice

Since the Hu-PBL-SCID mice are chimeras, they are susceptible to GVHD (Murphy et al., Eur. J. Immunol. 22:1421, 1992). Many of the Group 4 mice appeared to be suffering from a severe and fatal wasting disease within 3–5 weeks following engraftment. These mice manifested weight loss, ruffled fur and were pale before death. There was a correlation between successful engraftment, as determined by levels of CD3$^+$ cells, and the wasting disease. Those mice which remained healthy had low levels (<5%) of CD3$^+$ cells in their spleens when sacrificed 35–60 days after reconstitution. To determine the prevalence of this disease, 5 groups of SCID mice (4/group) were reconstituted with PBLs from 5 different PBL donors. At 32 days after engraftment, 15 of the mice (75%) had died. Mean survival time of the chimeric SCID mice engrafted with Hu-PBL was 25 days. This wasting disease was not seen in any mice in Groups 1, 2 or 3.

Histological examination of the liver, 18–24 days after injection of human PBLs in Group 4 mice, showed accumulations of inflammatory cells in the portal triads. There was a mixture of large and small lymphocytes, plasma cells and neutrophils without destruction of bile ducts. However, focal areas of parenchymal necrosis were present. In the lung, perivascular infiltrates of small and large lymphocytes were present. They were located around small arteries and veins and were associated with margination of neutrophils in the lumen of these vessels. Intra-alveolar hemorrhages were also present to a variable degree. The gastrointestinal tract and skin showed no significant abnormality. Therefore, evidence of GVHD was present in the lung and liver of Group 4 Hu-PBL-SCID mice but not in the skin and gut.

EXAMPLE 3

Human Primary Immune Response in Hu-PBL SCID Mice

Animals were engrafted using the method of the invention and the method of Mosier et al, supra, and were used to investigate the human lymphocyte-derived primary immune response to various antigens. The following materials and methods were used in the investigation.

Antigens

KLH was obtained from Calbiochem (La Jolla, U.S.A.). Surface coat protein of circumsporozoite malaria parasite (CSP) was provided by Hoffman-La Roche (Basel, Switzerland). The carbohydrate antigen Stn (AcNeu-α2-α6-Gal Nac-0) conjugated to KLH was provided by Biomira Inc., (Edmonton, Canada). Complete Freund's adjuvant (CFA) and incomplete Freund's adjuvant (IFA) were obtained from GIBCO (Betheseda, U.S.A.).

SCID Mice

SCID mice were bred and maintained as described in Example 1 herein. Briefly, homozygous C.B.-17 scid/scid (SCID) mice were bred and maintained in microisolator cages (original breeding pair from Dr. R. Phillips, Hospital for Sick Children, Toronto, Canada.) at the animal colony of the Samuel Lunenfeld Research Institute. Animals were fed autoclaved food and water and all manipulations of the mice were done under laminar flow. Mice were used when 4–10 weeks old.

Engraftment of SCID Mice with Hu-PBL

Human lymphocytes were isolated either from buffy coats, (provided by the Canadian Red Cross), or from whole blood from volunteers. Sera from blood donors were screened for antibodies to the antigens to be tested in the Hu-PBL-SCID mice. Only Hu-PBLs from donors who were antibody-negative, were used for SCID mice engraftment. The Hu-PBLs were isolated by Ficoll-Hypaque centrifugation (Pharmacia, Pistaway, U.S.A.) and injected i.p. (35–50× 10$^6$ PBLs/mouse) into the SCID mice under sterile conditions.

The SCID mice underwent one of two pretreatment procedures before engraftment of Hu-PBL, as follows:

(1) In the first procedure, the mice were pretreated 1 day prior to Hu-PBL injection with a single dose (20 μl i.p.) of anti-asialo GM-1 serum (Wako Chemicals, Dallas, Tex.). Anti-asialo GM 1 consists of rabbit polyclonal antibodies which recognize murine natural killer (NK) cells, and depletes NK activity when injected i.p. into the mice (Kasai, M. et al., Nature (Lond.) 291:334, 1981). Immediately prior to Hu-PBL engraftment SCID mice were irradiated, with a dose of 3 Gy γ-radiation, administered from a $^{137}$Cs source (Gamacell, Atomic Energy of Canada Ltd. Commercial Products). Irradiation alone had no effect on NK activity of SCID mouse splenocytes against YAC-1 mouse lymphoma target cells, as described above.

(2) In the second method the protocol described by Mosier et. al., Nature 335:256, 1988, was used for engraftment of Hu-PBLs. The SCID mice were injected i.p. with Hu-PBLs without pretreatment with irradiation and anti-ASGM-1 serum.

Assessment of Hu-PBL Engraftment in Hu-PBL-SCID Mice

Hu-PBL-SCID mice pretreated with anti-asialo GM-1 and radiation, were sacrificed 13 days after Hu-PBL engraftment and single cell suspensions were prepared from the spleens of individual mice. Red blood cells were lysed with hypotonic saline prior to FACS analysis for the presence of human lymphocytes. The following antibodies specific for human cell surface antigens were used: CD4, CD8, CD20 and CD45 (Becton Dickinson, Mountain View, U.S.A.). All antibodies were conjugated directly with either fluorescein isothiocyanate (FITC) or phycoerythrin (PE). The spleen cells (1–2×10$^5$ cells/sample) were incubated with the antibodies for 45 minutes on ice followed by three washes with FCS (2% v/v) in PBS. At least 5×10$^3$ cells were counted on an EPIC-C flow cytometer (Coulter Electronics). Spleen cells from non-reconstituted SCID mice were also analyzed by FACS, using the above antibodies. These cells were uniformly negative for staining with all of the anti-human lymphocyte markers used in this study.

Immunization of Hu-PBL-SCID Mice

SCID mice were engrafted with Hu-PBLs using the Mosier et al, 1988, supra, protocol. One day after engraftment the animals were vaccinated i.p. with 50 μg of KLH (in 100 μl of PBS) in 100 μl of CFA. Control animals were injected with PBS (100 μl) in 100 μl CFA.

SCID mice pretreated with anti-asialo GM-1 serum and radiation were engrafted with Hu-PBLs. One day after engraftment, the animals were immunized (i.p.) with 50 μg (in 100 μl of PBS) of antigen in 100 μl of adjuvant. The adjuvant consisted of CFA and IFA in a ratio of 1:10 (v/v). Control animals were injected with PBS (100 μl) in 100 μl of the adjuvant described above. These Hu-PBL-SCID mice were immunized with the antigens in a mixture of CFA and IFA, because approximately 50% of the animals died within 7 days of vaccination, when injected i.p. with antigen and CFA. Therefore, different mixtures of CFA and IFA were tested in Hu-PBL-SCID mice, and it was found that primary immune response to KLH could still be induced, when the antigen was injected in a adjuvant consisting of CFA and IFA in a ratio of 1:10 (v/v). Using this adjuvant mixture the premature death rate of the Hu-PBL-SCID mice pretreated with anti-asialo GM-1 and radiation was reduced to less than 10% in the first 7 days after vaccination. Blood was collected from the tail vein of the mice at various time intervals following vaccination, for analysis of human antigen specific antibodies.

Analysis of Hu-PBL-SCID Mice Sera for Human Antigen Specific Antibodies

Serum samples from human PBL donors and Hu-PBL-SCID mice were tested for human antigen-specific antibodies by ELISA as described by Markham and Donnenberg (Infection and Immunity 60:2305, 1992). Briefly, microwells (Immunlon 2;Dynatech) were coated with the antigen (0.2 μg per well) diluted in carbonate buffer (pH 9.6). The wells were then washed with PBS-Tween, and blocked with freeze dried milk (5% w/v) in PBS-Tween, followed by further three washes with PBS-Tween. Serial two-fold dilutions of sera were added to the microwells containing the bound antigen, and the plates were incubated overnight at 4° C. The plates were washed with PBS-Tween, and mouse anti-human IgG, or anti-human IgM alkaline phosphate conjugated antibodies (Caltag Laboratories, San Francisco, U.S.A.) were then added. After incubation for 2 h at room temperature, unbound conjugate was washed off with PBS-Tween and p-nitrophenylphosphate substrate (Sigma) was added to each well. Plates were incubated for 30 minutes at room temperature, then 3M sodium hydroxide was added to each plate and optical density was measured using an automated microplate plate reader at 410 nm (Dynatech MR600). Positive-control human sera from cancer patients immunized with Stn conjugated to KLH, were used with each KLH and Stn assay to ensure reproducibility between plates and assays. For the CSP assay, normal human serum was used as a control, to ensure reproducibility between plates and the assays.

The antibody titres of vaccinated Hu-PBL-SCID mice are expressed as the reciprocal of the highest dilution at which the optical density (O.D.) values (at 410 nm) were greater than those of non-vaccinated Hu-PBL-SCID mice. To detect human Stn antibodies in the sera from Stn vaccinated Hu-PBL-SCID mice, microtitre plates were coated with Stn conjugated to human serum albumin (from Biomira Inc. Edmonton). Control plates were coated with human serum albumin to test for cross-reaction of antibodies from Stn vaccinated Hu-PBL-SCID sera. No significant cross reaction was detected.

Kinetics of KLH Specific Human IgG Production in Hu-PBL-SCID Mice

SCID mice were pretreated with anti-asialo GM-1 serum and radiation before engraftment with Hu-PBLs. The time course of production for human anti-KLH IgG antibodies in the KLH-vaccinated and control Hu-PBL-SCID mice, was analyzed using test bleeds at 6, 9, 16 and 21 days post-Hu-PBL engraftment (results are given in FIG. 8).

Depletion of Human CD4 and CD8 Lymphocytes in Hu-PBL-SCID Mice

SCID mice were injected i.p. with 10 μg of mouse $IgG_{2a}$ anti-human CD4 (3 groups of 5 mice) or CD8 (3 groups of 5 mice) or CD14 antibodies (Amac Inc. Westbrook, U.S.A.). The next day, SCID mice treated with anti-human CD8 (2 groups) and CD4 (2 groups) antibodies were engrafted, using our Hu-PBL engraftment protocol. One day after engraftment, one group each of Hu-PBL-SCID mice depleted of CD4 and CD8 lymphocytes were vaccinated with KLH in adjuvant as described above, and one group each of Hu-PBL-SCID mice depleted of CD4 and CD8 cells were injected with PBS in adjuvant.

Spleen cells from the SCID mice and Hu-PBL-SCID mice treated with anti-human CD4, CD8 and CD14 antibodies were analyzed by FACS for human CD4 and CD8 cells (representative FACS profiles are shown in FIG. 10), and the sera from the Hu-PBL-SCID mice depleted of human CD4 and CD8 cells were analyzed for human anti-KLH antibodies (results given in FIG. 11).

Results

The major limitation of the Hu-PBL-SCID engraftment procedure of Mosier et al, 1988, supra, is the low level of engraftment of human lymphocytes in SCID mice lymphoid tissues, eg. spleen, and lymph nodes (Martino, G. et al., Eur. J. Immunol. 23:1023, 1993). Substantially higher levels of Hu-PBL engraftment can be achieved in the SCID mice spleen using procedure 1 which consists of firstly, administrating only a single dose of anti-asialo GM-1 serum to the SCID mice (rather than one every 5–7 days as in Example 1 herein), and secondly, a lower dose of anti-asialo GM-1 serum was used compared to the procedure in Example 1 (20 μl instead of 25 μl). Using protocol 1, the levels of engraftment of human CD4, CD8, CD45 and B cells in the SCID mice spleens are shown in Table 5. These results are similar to those reported in example 1 herein and are substantially higher than those achieved by Martino et al. (Eur. J. Immunol. 23:1023) who used the Mosier et. al., 1988, supra, protocol. The lifespan of these anti-asialo GM-1 and radiation treated Hu-PBL-SCID mice is in the range of 21–28 days, which is markedly different from the lifespan of SCID mice engrafted with Hu-PBLs by the Mosier technique which can be up to six months (Saxon, A. et al J. Clin. Invest. 87:658, 1991 and; Tary-Lehman, M. and Saxon, A. J. Exp. Med. 175:503, 1992). Death of the highly engrafted Hu-PBL-SCID mice results mainly from graft versus host disease (GVHD), as assessed by histology, with weight loss, ruffled fur and hunched back.

In preliminary studies Hu-PBL were engrafted into SCID mice using the Mosier et al. protocol, these Hu-PBL-SCID mice were then vaccinated the following day with KLH mixed with CFA, or with PBS in CFA (control mice). The mice were bled 14–16 days after vaccination, and the sera analyzed for human anti-KLH, IgG and IgM antibodies. As reported by Markham and Donnenberg (Inf. & Immun. 60:2305, 1992) no difference was found in the levels of human anti-KLH, IgM or IgG antibodies in the vaccinated and control mice. These negative results prompted us to induce human primary immune response in Hu-PBL-SCID mice pretreated with anti-asialo GM-1 serum and radiation. Three antigens (KLH, CSP and Stn) were tested for induction of human primary immune response in these mice, using Hu-PBLs from several donors, who had tested antibody negative for these antigens. Using the first Hu-PBL engraftment protocol outlined above, the mice were bled 14–16 days after vaccination and the sera tested by ELISA for specific human IgG and IgM antibodies. Results from representative vaccination experiments are shown in FIG. 9.

Figure 12:
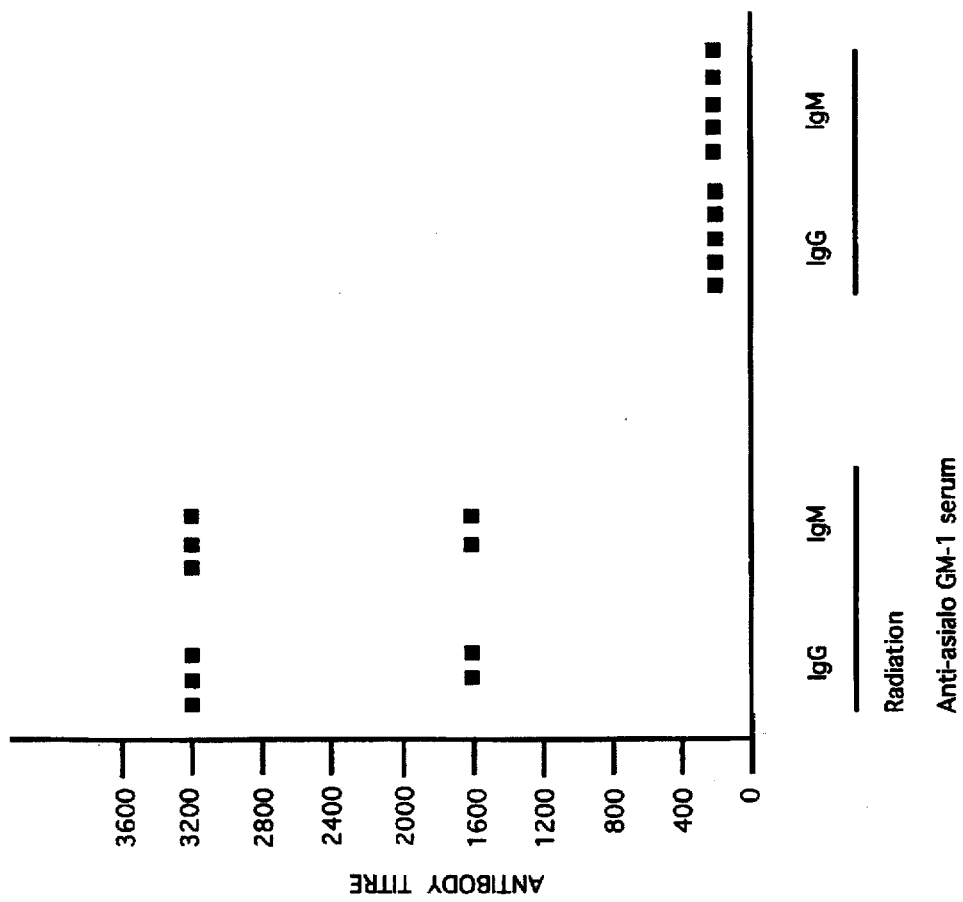

FIG. 9 shows the anti-KLH, CSP and Stn human antibody response. Hu-PBL-SCID mice (5 mice per group) were engrafted with Hu-PBLs from donors that tested IgG and IgM negative for KLH, CSP and Stn. One day after Hu-PBL engraftment, the mice were vaccinated i.p. with either KLH, Stn or CSP mixed with adjuvant, and a control group of Hu-PBL-SCID mice were injected i.p. with PBS mixed adjuvant. All mice were bled 14–16 days following vaccination. Human anti-KLH, CSP and Stn IgG and IgM antibody levels were measured by ELISA. The antibody titres of vaccinated Hu-PBL-SCID mice are expressed as the reciprocal of the highest serum dilution at which the optical density values (at 410 nm) of the vaccinated mice was greater than that of the control group. FIG. 12 shows the lack of anti-KLH response achieved with Mosier protocol mice.

The results show that all of the vaccinated Hu-PBL-SCID mice produced human IgG and IgM antibodies against the three antigens. Hu-PBL-SCID mice, not vaccinated with the three antigens, had only background levels of human IgG and IgM antibody titres for these antigens, and the antibody titres in the vaccinated animals were substantially higher than those of the non-vaccinated mice. The IgM and IgG antibodies produced against Stn, CSP and KLH showed no significant cross reactivity, suggesting that the immune response was antigen specific. In the immunized Hu-PBL-SCID the ratio of human anti-KLH, CSP Stn specific IgM to IgG varies from 0.5 to 2. The KLH protein induced the highest human IgG and IgM titres (compared to Stn and CSP). The pattern of antibody responses by Hu-PBL-SCID mice to the three antigens is similar to that observed in humans after vaccination with these same three antigens. In humans KLH has been shown to be highly immunogenic (Markham and Donnenberg, 1992, supra), while Stn (MacLean, G. D. et al, Cancer Immunol. Immunother., in press) and CSP (Herrington, D. A. et al, Bull WHO, 68(Supp.):33, 1990) have very low immunogenicity and induce low titres of IgG and IgM antibodies.

Data from human vaccination studies using Stn and CSP antigens show that several vaccinations are required before a significant antibody response can be stimulated to these antigens, but similar titres of human IgG and IgM for CSP and Stn in Hu-PBL-SCID mice can be induced after a single vaccination. The reasons for this difference is not clear but may it be related to the use of CFA adjuvant in our SCID mice model, or to the route of vaccination, in addition, it is possible that the SCID mouse environment enhances the human lymphocyte-mediated antibody response to these antigens.

The half-lives of human IgM and IgG in Hu-PBL-SCID mice are 39.5 and 276 hours respectively (Abedi, M. R. et al Eur. J. Immunol. 22:823, 1992 and; Saxon, A. et al, J. Clin. Invest. 87:658, 1991). Assuming that similar kinetics of human IgG and IgM clearance apply in our Hu-PBL-SCID mice model, then the estimated levels of IgM synthesis specific for KLH, CSP and Stn are actually considerably higher than those of IgG. If corrections were made to the antibody titres in FIG. 9, for the difference in the half-lives of human IgG and IgM in Hu-PBL-SCID mice, then the first vaccination with these three antigens induces a mainly IgM antibody response.

Kinetic studies of human anti-KLH IgG production in Hu-PBL-SCID mice vaccinated with KLH (FIG. 8) show that a plateau of anti-KLH antibody production was reached 14–16 days after Hu-PBL engraftment. As indicated earlier, survival time of the Hu-PBL-SCID mice is limited to 21–28 days, therefore serum samples could not be obtained for all the animals beyond 21 days.

FIG. 8 shows the Kinetics of human IgG anti-KLH response. SCID mice were engrafted with Hu-PBLs from donors that were negative for KLH antibodies. Time A, is the day of engraftment of Hu-PBLS in SCID mice (2 groups of 5 animals were engrafted). At time B one group of mice were vaccinated i.p. with KLH and adjuvant (experimental group; 0) or PBS with adjuvant (control group;). The mice were bled on day 6, 9, 16 and 21 after Hu-PBL engraftment, and sera analyzed by ELISA. Data shown are the mean values of optical density (at 410 nm) for vaccinated and control mice ±SEM.

To investigate the function of human T helper ($T_h$;CD4), cytotoxic T cells (CTLs;CD8) and macrophages (CD14) in the induction of primary immune response in Hu-PBL-SCID mice, these two cell populations were depleted by i.p. injection of SCID mice, with mouse anti-human CD4, CD14 or CD8 antibodies, prior to Hu-PBL engraftment and KLH vaccination. The spleen cells from SCID and Hu-PBL-SCID mice were isolated and analyzed by FACS for CD4 and CD8 lymphocytes. Representative FACS profile of cells from Hu-PBL-SCID spleens are shown in FIG. 10, and the antibody titres for human anti-KLH antibodies in mice depleted of human CD4 or CD8 lymphocytes are shown in FIG. 11.

FIG. 10 shows the FACS profile of human CD4 and CD8 lymphocytes, isolated from the spleens of SCID and Hu-PBL-SCID mice. The Lymphocytes were labelled with either mouse anti-human CD4 antibody conjugated with FITC or mouse anti-human CD8 antibody conjugated with PE. Panel A and B shows the FACS profile of human CD4 (panel A) and CD8 (panel B) lymphocytes from SCID mice. Panel C and E show the FACS profile of human CD8 (panel C) and CD4 (panel E) cells from Hu-PBL-SCID mice. Panel D and F show the FACS profile of human CD8 (panel D) and CD4 (panel F) lymphocytes from Hu-PBL-SCID mice after treatment with either anti-human CD8 (panel D), or anti-human CD4 (panel F) antibodies.

FIG. 11 shows the human anti-KLH antibody response in Hu-PBL-SCID mice. Hu-PBL-SCID mice (5 mice per group) were depleted of either human CD4 or CD8 cells by i.p. injection with either mouse anti-human CD4 or CD8 antibodies, 24 h before engraftment with Hu-PBLs. Once day after Hu-PBL engraftment the CD4 and CD8 depleted mice were vaccinated i.p. with either KLH in adjuvant (vaccinated animals), or with PBS alone in adjuvant (control animals). Mice were bled 14–16 days after vaccination. Human anti-KLH, IgG and IgM levels were measured by ELISA. The antibody titres of KLH vaccinated animals are expressed as the reciprocal of the highest serum dilution at which the optical density values (at 410 nm) of the vaccinated mice sera is above that of the control group. Mice depleted of human macrophages had 3.5 times lower titres of KLH IgM compared to control animals.

FACS analysis showed no detectable levels of CD4 cells, in the spleens of mice treated with anti-human CD4 antibody, but CD8 cells were still present (in the range of: 10 to 20%). No human anti-KLH IgG or IgM antibodies were detected in the serum of animals depleted of CD4 cells (FIG. 11). However, mice depleted of CD8 cells continued to produce normal levels of human anti-KLH IgG and IgM antibodies (FIG. 11). FACS analysis of the spleens cells from animals treated with human anti-CD8 antibody showed the depletion of CD8 cells, however, CD4 cells were still present (in the range: 42 to 77%). The FACS data from CD4 and CD8 depleted mice shows that mouse anti-human CD4 and CD8 depleted mice shows that mouse anti-human CD4 and CD8 antibodies were specific in their in vivo deletion activities, and this selective depletion technique could be used to investigate the roles of human lymphocytes (including NK, macrophage and B cells) in the various human immune functions in the Hu-PBL-SCID mice.

The levels of human CD4 cells (44–77%) in the KLH vaccinated Hu-PBL-SCID mice are considerably higher than the non-vaccinated mice (18.53%; Table 1), suggesting that vaccination of Hu-PBL-SCID mice with KLH and adjuvant induces substantial proliferation of CD4 cells. Proliferation of CD4 cells in Hu-PBL-SCID mice spleen has also been observed in human secondary immune response, as described above. In contrast, the levels of CD8 in the spleens of KLH vaccinated (10–20%) and non-vaccinated (19.13% ; see Table 5) mice was similar.

Taken together these data demonstrates the essential function of human $T_h$ cells in the human primary immune response, and this function can be clearly demonstrated in our Hu-PBL-SCID model. The human CD4 cell proliferation data, along with human anti-KLH IgM and IgG antibodies production results, suggests that human effector T cells, antigen presenting cells, and B cells are functional in the Hu-PBL-SCID mice environment. The data on the selective depletion of human lymphocytes in the Hu-PBL-SCID mouse demonstrates that the transplanted Hu-PBLs can be manipulated in the SCID mice yet retain their predicted immune functions. The ability to perform selective depletion of subsets of lymphocytes in the Hu-PBL-SCID mice in vivo is important for the use of this model to study GVHD, and to prolong the survival time of the reconstituted mice in order to induce primary and secondary antibody responses in the same animal, and a plethora of other immunological phenomenon using human cells for which no other similar method exists to date. The severity of GVHD was less in chimeric mice depleted of human B lymphocytes or macrophages. Chimeric mice depleted of human macrophages or B cells had a mean survival time of 38 or 50 days respectively.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the invention.

All publications and patent applications cited in this specification are herein incorporated by reference as if each individual publication or patent application were specifically and individually indicated to be incorporated by reference.

TABLE 1

Number of mononuclear cells in spleens of SCID mice following pretreatment with radiation, anti-ASGM1 and reconstitution with human PBLs[a]

| treatment | mean (±SEM) number of spleen cells (× 10^6) | n |
|---|---|---|
| normal SCID mouse (no pretreatment) | 6.2(2.9) | 6 |
| radiation (d12) | 3.1(0.9) | 4 |
| anti-ASGM1 (d12) | 4.5(0.9) | 4 |
| radiation + anti-ASGM1 (d12) | 2.5(0.1) | 3 |
| radiation + anti-ASGM1 + PBLs (d6–8) | 7.6(1.0) | 5 |

TABLE 1-continued

Number of mononuclear cells in spleens of SCID mice following pretreatment with radiation, anti-ASGM1 and reconstitution with human PBLs[a]

| treatment | mean (±SEM) number of spleen cells (× 10^6) | n |
|---|---|---|
| radiation + anti-ASGM1 + PBLs (d12–14) | 26.0(4.6) | 21 |
| radiation + anti-ASGM1 + PBLs (d18–24) | 8.2(2.4) | 6 |

[a] SCID mice were sacrificed on the days indicated following pretreatment.
Pretreatments: radiation, 3 Gy; anti-ASGM1, 25 μl i.p. every 5–7d; PBLs, 3.3–5.0 × 10^7 Ficoll-separated PBLs i.p.
In the case of mice given radiation + anti-ASGM1 + PBLs, the first dose of anti-ASGM1 was given the day before PBL injection and the radiation administered immediately prior to PBL injection.

TABLE 2

Cell surface phenotype of human lymphocytes in spleens of pretreated hu-PBL-SCID mice[a]

| Phenotype | mean % positive cell (±SEM) |
|---|---|
| TcRαβ | 47.0 (9.7) |
| TcRγδ | 2.4 (0.6) |
| CD45 | 80.4 (11.4) |
| CD16/56 | 8.2 (2.4) |
| CD20 | 17.2 (3.2) |

[a] SCID mice were pretreated with 3 Gy radiation plus 25 μl anti-ASGM1, and reconstituted with human PBLs. anti-ASGM1 was administered every 5–7 days after PBL injection. Mice were sacrificed on days 6–32 following PBL injection and splenocytes analysed by FCM.

TABLE 3

Intra and inter donor variability in engraftment of hu-PBL-SCID mice[a]

| Human PBL Donor | mean (±SEM) % CD3 + cells in spleens |
|---|---|
| 1 | 57.2 (2.2) |
| 2 | 52.4 (5.1) |
| 3 | 28.6 (11.7) |
| 4 | 23.4 (9.6) |
| 5 | 41.2 (11.2) |

[a] SCID mice (3–4/group with each donor) were pretreated as in Table 2 and sacrificed 12–14 days following PBL injection. Splenocytes were analysed by FCM.

TABLE 4

In vitro proliferative response of hu-PBL-SCID splenocytes to PHA[a] cpm, mean (±SEM)

| hu-PBL-SCID mouse | −PHA | +PHA |
|---|---|---|
| 1 | 378 (21) | 17935 (9121) |
| 2 | 290 (82) | 13579 (486) |
| 3 | 428 (96) | 15755 (931) |
| 4 | 548 (58) | 16691 (1773) |

[a] SCID mice were pretreated as in Table 2 and sacrificed on day 14 following PBL injection. RBC depleted splenocytes from these mice (0.5 × 10^5 cells) were incubated with fresh, irradiated (30 Gy) autologous human PBL feeders (0.5–1.0 × 10^5 cells). PHA was added at a concentration of 1.0–5.0 μg/ml. Replicates of 3–6 wells were used in each experiment. Plates were incubated for 4 days then pulsed with 1μCi ^3H-thymidine. After 16 hours, the wells were washed, and incorporated ^3H-thymidine measured in a β counter.

TABLE 5

Cell surface phenotype of human lymphocytes in the spleens of Hu-PBL-SCID mice pretreated only with anti-asialo GM-1 serum and radiation.

| Phenotype | Mean % Hu-PBL positive cells (SEM) |
|---|---|
| CD20 | 17.04 (3.84) |
| CD4 | 18.53 (3.74) |
| CD8 | 19.13 (3.40) |
| CD45 | 69.76 (8.63) |

The SCID mice (6 animals in each group) were sacrificed 13 days following Hu-PBL engraftment Hu-PBLs from Hu-PBL-SCID mice spleens were analyzed by FACS.

We claim:

1. A chimeric SCID mouse having at least 70% reconstitution of functional human lymphocytes in the spleen; having reconstitution of human macrophages in the spleen; and having at least 5% reconstitution of functional human NK cells in the spleen; exhibiting a human primary and secondary humoral response and a cellular immune response to a preselected antigen introduced into the chimeric mammal; and exhibiting severe xenogenic human graft versus host disease.

2. A chimeric mouse as claimed in claim 1 substantially deficient in human CD4+, CD8+ or CD14+ human cells.

3. A chimeric mouse as claimed in claim 1 wherein the spleen comprises 25 to 75% CD3+ cells, 10 to 25% CD20+ cells, 5 to 15% CD16/56+ cells, 35 to 60% TcRab+cells and 1 to 5% TcRag+cells.

4. A chimeric mouse as claimed in claim 1 wherein the human primary humoral immune response comprises the production of specific human IgM and IgG antibodies in response to immunization of the chimeric mouse with an antigen.

5. A chimeric SCID mouse obtained by engraftment of human peripheral blood leukocytes into an immunocompromised SCID mouse, pretreated with irradiation and with an antibody directed to the mouse's natural killer cells, having at least 70% reconstitution of functional human lymphocytes in the spleen; having reconstitution of human macrophages in the spleen; and having at least 5% reconstitution of functional human NK cells in the spleen; exhibiting a human primary and secondary humoral response and a cellular immune response to a preselected antigen introduced into the chimeric mammal; and exhibiting severe xenogenic human graft versus host disease.

6. A chimeric mouse as claimed in claim 5 wherein the immunocompromised mouse is substantially depleted of functional T and B lymphocytes.

7. A chimeric mouse as claimed in claim 5 wherein the severe xenogenic human graft versus host disease exhibits within two to five weeks after engraftment.

8. A chimeric mouse as claimed in claim 1 wherein the mouse is reconstituted with 3 to $5 \times 10^7$ human peripheral blood leukocytes.

9. A chimeric SCID mouse as claimed in claim 5 wherein the antibody is anti-ASGM1.

10. A chimeric SCID mouse as claimed in claim 5 wherein the immunocompromised SCID mouse is engrafted with 3 to $5 \times 10^7$ human peripheral blood leukocytes.

11. A chimeric SCID mouse as claimed in claim 1, wherein the mouse is reconstituted with 3 to $5 \times 10^7$ human peripheral blood leukocytes.

12. A chimeric SCID mouse as claimed in claim 1 having between 5 and 15% reconstitution of functional human NK cells in the spleen.

13. A chimeric SCID mouse as claimed in claim 5 having between 5 and 15% reconstitution of functional human NK cells in the spleen.

* * * * *